US009797883B2

(12) United States Patent
Shim et al.

(10) Patent No.: US 9,797,883 B2
(45) Date of Patent: Oct. 24, 2017

(54) RE-TRAFFICKING OF HERG REVERSES LONG QT SYNDROME 2 PHENOTYPE IN HUMAN IPS-DERIVED CARDIOMYOCYTES

(71) Applicant: Singapore Health Services Pte Ltd, Singapore (SG)

(72) Inventors: Winston Se Ngie Shim, Singapore (SG); Ashish Mehta, Singapore (SG); Chrishan Julian Alles Ramachandra, Singapore (SG); Philip En Hou Wong, Singapore (SG)

(73) Assignee: Singapore Health Services Pte Ltd, Singapore (SG)

( * ) Notice: Subject to any disclaimer, the term of this patent is extended or adjusted under 35 U.S.C. 154(b) by 0 days.

(21) Appl. No.: 14/776,616

(22) PCT Filed: Mar. 14, 2014

(86) PCT No.: PCT/SG2014/000129
§ 371 (c)(1),
(2) Date: Sep. 14, 2015

(87) PCT Pub. No.: WO2014/142760
PCT Pub. Date: Sep. 18, 2014

(65) Prior Publication Data

US 2016/0033481 A1 Feb. 4, 2016

(30) Foreign Application Priority Data

Mar. 15, 2013 (SG) ................................. 201301987

(51) Int. Cl.

| | |
|---|---|
| ***G01N 33/50*** | (2006.01) |
| ***A61K 31/443*** | (2006.01) |
| ***A61K 38/06*** | (2006.01) |
| ***G01N 27/416*** | (2006.01) |

(52) U.S. Cl.
CPC ....... *G01N 33/5061* (2013.01); *A61K 31/443* (2013.01); *A61K 38/06* (2013.01); *G01N 27/416* (2013.01)

(58) Field of Classification Search
None
See application file for complete search history.

(56) References Cited

FOREIGN PATENT DOCUMENTS

WO WO-2007/002972 A2 1/2007

OTHER PUBLICATIONS

Anderson et al., "Most LQT2 mutations reduce Kv11.1 (hERG) current by a class 2 (trafficking-deficient) mechanism," Circulation. 113(3):365-73 (2006).
Bellin et al., "Isogenic human pluripotent stem cell pairs reveal the role of a KCNH2 mutation in long-QT syndrome," EMBO J. 32(24):3161-75 (2013).
Bellocq et al., "A common antitussive drug, clobutinol, precipitates the long QT syndrome 2," Mol Pharmacol. 66(5):1093-102 (2004).
Dausse et al., "A mutation in HERG associated with notched T waves in long QT syndrome," J Mol Cell Cardiol. 28(8):1609-15 (1996).
Elbashir et al., "Analysis of gene function in somatic mammalian cells using small interfering RNAs," Methods. 26(2):199-213 (2002).
Ficker et al., "Retention in the endoplasmic reticulum as a mechanism of dominant-negative current suppression in human long QT syndrome," J Mol Cell Cardiol. 32(12):2327-37 (2000).
Ficker et al., "Role of the cytosolic chaperones Hsp70 and Hsp90 in maturation of the cardiac potassium channel HERG," Circ Res. 92(12):e87-100 (2003).
Gill et al., "Losing heart: the role of apoptosis in heart disease—a novel therapeutic target?" FASEB J. 16(2):135-46 (2002).
Gonçalves et al., "Activation of calpain-1 in human carotid artery atherosclerotic lesions," BMC Cardiovasc Disord. 9:26 (2009) (6 pages).
Guo et al., "Cell surface expression of human ether-a-go-go-related gene (hERG) channels is regulated by caveolin-3 protein via the ubiquitin ligase Nedd4-2," J Biol Chem. 287(40):33132-41 (2012) (21 pages).
International Preliminary Report on Patentability and Written Opinion for International Patent Application No. PCT/SG2014/000129, issued Sep. 15, 2015 (10 pages).
International Search Report for International Patent Application No. PCT/SG2014/000129, mailed Mar. 11, 2014 (8 pages).
Itzhaki et al., "Modelling the long QT syndrome with induced pluripotent stem cells," Nature. 471(7337):225-9 (2011).
Iwai et al., "Hsp90 prevents interaction between CHIP and HERG proteins to facilitate maturation of wild-type and mutant HERG proteins," Cardiovasc Res. 100(3):520-8 (2013).
Kagan et al., "The dominant negative LQT2 mutation A561V reduces wild-type HERG expression," J Biol Chem. 275(15):11241-8 (2000).
Lahti et al., "Model for long QT syndrome type 2 using human iPS cells demonstrates arrhythmogenic characteristics in cell culture," Dis Model Mech. 5(2):220-30 (2012).
Leu et al., "A small molecule inhibitor of inducible heat shock protein 70," Mol Cell. 36(1):15-27 (2009).
Matsa et al., "Drug evaluation in cardiomyocytes derived from human induced pluripotent stem cells carrying a long QT syndrome type 2 mutation," Eur Heart J. 32(8):952-62 (2011).
Mehta et al., "Assessment of drug induced developmental toxicity using human embryonic stem cells," Cell Biol Int. 32(11):1412-24 (2008).
Mehta et al., "Intrinsic properties and external factors determine the differentiation bias of human embryonic stem cell lines," Cell Biol Int. 34(10):1021-31 (2010).

(Continued)

*Primary Examiner* — John Ulm
(74) *Attorney, Agent, or Firm* — Clark & Elbing LLP

(57) ABSTRACT

The present invention relates to generating hiPSC-derived cardiomyocytes and embryoid bodies that recapitulate the disease phenotype of Long QT Syndrome and their use in developing pharmacological treatments thereof. The present invention also includes the use of a compound which inhibits the ubiquitin-proteasome pathway for the preparation of a medicament for the prophylaxis or treatment of a disease associated with prolonged ventricular repolarization (cardiac arrhythmia) caused by one or more mutations in the amino acid sequence of the hERG potassium channel.

12 Claims, 22 Drawing Sheets

(56) References Cited

OTHER PUBLICATIONS

Mehta et al., "Pharmacological response of human cardiomyocytes derived from virus-free induced pluripotent stem cells," Cardiovasc Res. 91(4):577-86 (2011).
Mehta et al., "Re-trafficking of hERG reverses long QT syndrome 2 phenotype in human iPS-derived cardiomyocytes," Cardiovasc Res. 102(3):497-506 (2014).
Patel et al., "Pharmacological approach to the treatment of long and short QT syndromes," Pharmacol Ther. 118(1):138-51 (2008).
Priori et al., "Genetic and molecular basis of cardiac arrhythmias; impact on clinical management. Study group on molecular basis of arrhythmias of the working group on arrhythmias of the european society of cardiology," Eur Heart J. 20(3):174-95 (1999).
Priori et al., "Low penetrance in the long-QT syndrome: clinical impact," Circulation. 99(4):529-33 (1999).
Sanguinetti et al., "hERG potassium channels and cardiac arrhythmia," Nature. 440(7083):463-9 (2006).
Shieh et al., "Potassium channels: molecular defects, diseases, and therapeutic opportunities," Pharmacol Rev. 52(4):557-94 (2000).
Smith et al., "Calpains, mitochondria, and apoptosis," Cardiovasc Res. 96(1):32-7 (2012).
Sorimachi et al., "Regulation and physiological roles of the calpain system in muscular disorders," Cardiovasc Res. 96(1):11-22 (2012).
Thomas et al., "Defective protein trafficking in hERG-associated hereditary long QT syndrome (LQT2): molecular mechanisms and restoration of intracellular protein processing," Cardiovasc Res. 60(2):235-41 (2003).

LQTS2 Arrhythmic eposide

Groups
1: hESC, H9
2: Control-hiPSC
3: LQTS2-hiPSC1
4: LQTS2-hiPSC2
5: human dermal fibroblast
M: DNA ladder
+: Positive control Paced at 1 Hz
Control
LQTS2
Ventricular
0mV
Atrial
0mV
200 ms +40mV
-40mV
i
Total $I_K$
ii
E-4031
iii
$I_{Kr}$ (i-ii)
5 pA/pF
1s
Control
LQTS2

Ventricular
Atrial
Control
LQTS2
APD (ms)

Peak Current
Tail Current
Control
LQTS2
Voltage (mV)

200 μV
1s
Ventricular EAD
40mV
2s
0.4s

Control
LQTS2
FPD
200 μV
200 ms
cFPD (sec)
p<0.001
Cntrl
LQTS2

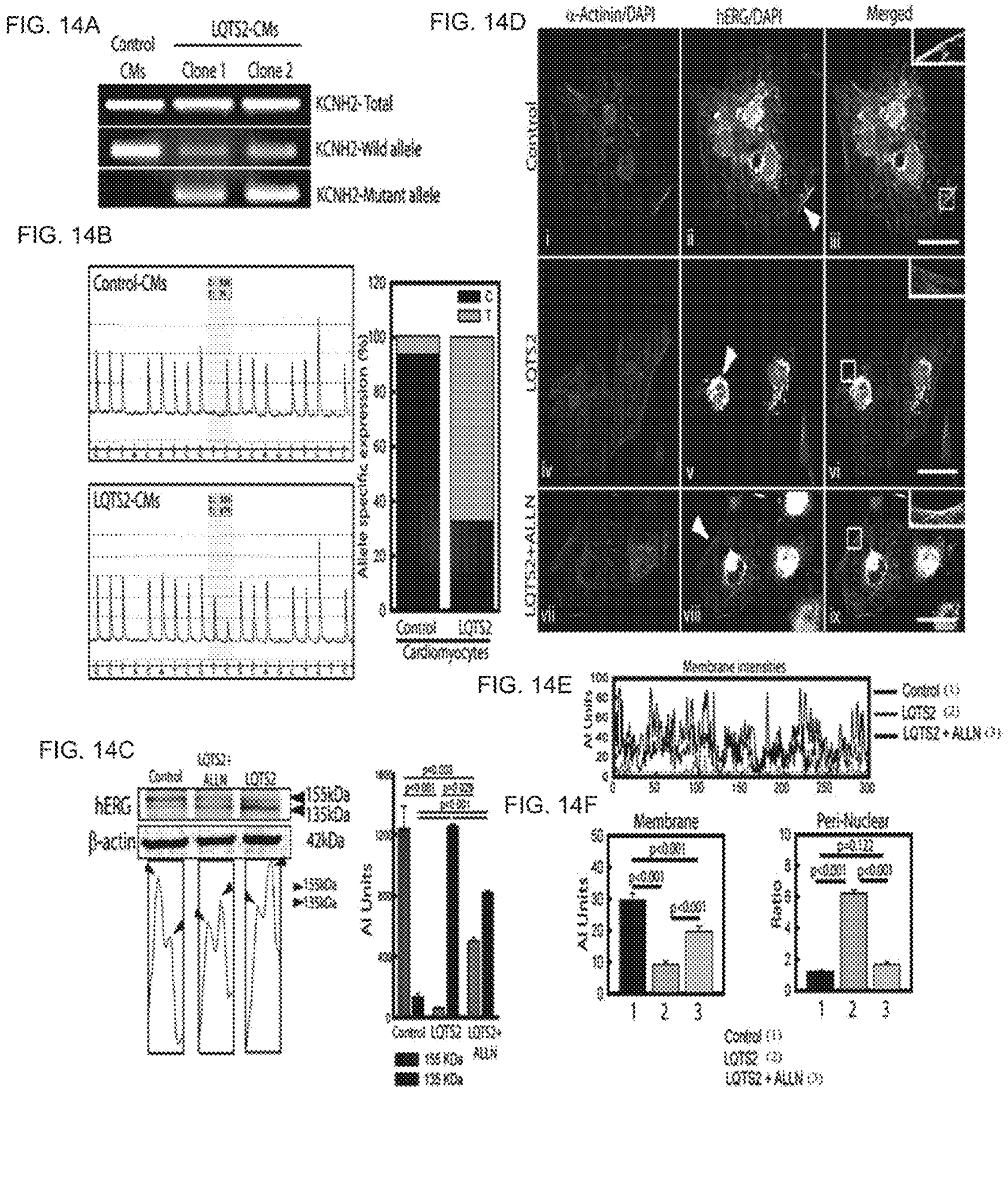
FIG. 14A
Control CMs
LQTS2-CMs
Clone 1
Clone 2
KCNH2- Total
KCNH2-Wild allele
KCNH2-Mutant allele
FIG. 14B
Control-CMs
LQTS2-CMs
Allele specific expression (%)
C
T
Control
LQTS2
Cardiomyocytes
FIG. 14C
Control
LQTS2+ ALLN
LQTS2
hERG
β-actin
155kDa
135kDa
42kDa
AI Units
155 KDa
135 KDa
FIG. 14D
α-Actinin/DAPI
hERG/DAPI
Merged
Control
LQTS2
LQTS2+ALLN
FIG. 14E
Membrane intensities
AI Units
Control (1)
LQTS2 (2)
LQTS2 + ALLN (3)
FIG. 14F
Membrane
Peri-Nuclear
AI Units
Ratio
Control (1)
LQTS2 (2)
LQTS2 + ALLN (3)

LQTS2
LQTS2 + ALLN (42h)
50mV
10s p=0.013
p=0.005
p<0.001
cFPD (sec)
C
0h 18h 42h
LQTS2 p<0.001
p<0.001
p=0.987
Beating Frequency (Hz)
0h 18h 42h

Paced at 1 Hz
LQTS2
LQTS2+ALLN
Ventricular
0mV
Atrial
20mV
200ms

Ventricular
Atrial
APD (ms)

LQTS2+ALLN
+40 mV
-40 mV
-50 mV
i
ii
iii
5 pA/pF
1 s

Control
LQTS2
LQTS2+ALLN
density (pA/pF)
Voltage (mV)

Control
LQTS2
LQTS2+ALLN
activation curve
Voltage (mV)

Slope factor
Groups
Control (1)
LQTS2 (2)
LQTS2+ALLN (3)

RE-TRAFFICKING OF HERG REVERSES LONG QT SYNDROME 2 PHENOTYPE IN HUMAN IPS-DERIVED CARDIOMYOCYTES

FIELD OF THE INVENTION

The present invention relates to genetic disorders caused by mutations in ion channel subunits. More particularly, the invention relates to generating hiPSC-derived cardiomyocytes and embryoid bodies that recapitulate the disease phenotype of Long QT Syndrome and their use in developing pharmacological treatments thereof.

BACKGROUND OF THE INVENTION

Hereditary long QT syndrome (LQTS) is a genetic disorder caused by mutations in one or more ion channel subunits expressed in the heart. LQTS is characterized by delayed or prolonged cardiac repolarization in electrocardiogram with increased risks of developing polymorphic ventricular tachycardia (torsade de pointes, TdP), syncope and sudden cardiac death. To date, LQTS has been associated with over 500 different mutations in at least 13 genes encoding cardiac ion channel proteins. Genotype to phenotype penetrance is estimated to be 60-70% depending on location of the mutation, with more severe phenotypes arising from mutations around the pore-forming regions Matsa E, et al., *Eur Heart J* 2011; 32: 952-962).

LQTS2 implicates hERG (human ether-a-go-go related gene), a gene (KCNH2) that codes for a protein known as $K_v$11.1, which constitutes the pore-forming α subunit of the rapidly-activating delayed rectifier potassium current ($I_{Kr}$). Heterozygote KCNH2 mutations exert a dominant-negative effect on wild-type hERG channel associated $I_{Kr}$ currents (Thomas D, et al., *Cardiovascular research* 2003; 60:235-241; Shieh C C, et al., *Pharmacological reviews* 2000; 52:557-594) by impaired trafficking pathways or altered channel kinetics of the resulting co-assembled hERG heterotetramers. Current non-cardiac heterologous expression systems in HEK 293 or CHO cells have implicated endoplasmic reticulum (ER) sequestering of hERG (Thomas D, et al., *Cardiovascular research* 2003; 60:235-241; Ficker E, et al., *Journal of molecular and cellular cardiology* 2000; 32:2327-2337) as a probable cause of LQTS2 manifestation (Thomas D, et al., *Cardiovascular research* 2003; 60:235-241). However, inability to accurately model the disease in heterologous systems (Itzhaki I, et al., *Nature* 2011; 471: 225-229) and the lack of in vitro humanized diseased cardiomyocytes (CMs) have significantly hindered a true mechanistic understanding of this disease.

Disease-specific induced pluripotent stem cells offer a unique opportunity for disease modeling. Such models yield previously unavailable insights into the molecular basis of disease manifestations that could serve as an invaluable platform for risk stratification and drug discovery. In this study, we show that CMs derived from LQTS2 patient-specific (A561V mutant) hiPSC recapitulate the disease phenotype with defective trafficking of hERG channel in vitro and demonstrate phenotypic reversal through pharmacological intervention of ER-Golgi export machinery.

This is the first time being shown that such allelic dominance is only manifesting itself in cardiomyocytes and not in other unrelated cells in the same patient. Therefore, this pathology and potential treatment of LQTS2 can only be studied and demonstrated in cardiomyocytes where the disease originated in the first place, but not in other cellular systems from the same patient such as the original patient skin fibroblasts or their undifferentiated iPSC-derived from the said fibroblasts.

SUMMARY OF THE INVENTION

Modeling monogenic arrhythmogenic diseases using induced pluripotent stem cells (hiPSC) offers unprecedented mechanistic insights into disease pathogenesis. We utilized LQTS2-hiPSC derived cardiomyocytes to elucidate pathological changes and to demonstrate reversal of LQTS2 phenotype in a therapeutic intervention.

An aspect of the invention provides a method for testing compounds for activity in ameliorating an LQTS2 phenotype in a cell or animal, comprising the steps;

(a) contact LQTS2-specific cardiomyocytes or embryoid bodies (EBs) with the compound, and (b) quantitate the level of hERG protein in the endoplasmic reticulum (ER) and in the sarcolemma, and compare the relative level of hERG in the ER and sarcolemma with untreated cardiomyocytes or EBs, wherein an increase in sarcolemma level and a decrease in ER level of hERG in the treated cardiomyocytes or EBs indicates re-trafficking of hERG and the compound has LQTS2-ameliorating activity, and/or (c) quantitate the level of glycosylated (mature) hERG protein and compare with untreated cardiomyocytes or EBs, wherein increased glycosylation indicates the compound has LQTS2-ameliorating activity, and/or (d) measure the local field potential duration (FPD), correct for the beating rate of contracting areas (cFPD), and compare with untreated cardiomyocytes or EBs, wherein a time-dependent reduction in cFPD indicates the compound has LQTS2-ameliorating activity, and/or (e) measure the action potential duration (APD), and compare with untreated cardiomyocytes or EBs, wherein a time-dependent reduction in APD indicates the compound has LQTS2-ameliorating activity.

In a preferred embodiment, the method comprises a further step of culturing the LQTS2-specific cardiomyocytes or EBs until they are spontaneously contracting or induced to contract.

A preferred embodiment of the method is directed towards when the phenotype is cardiac rhythm disturbance in LQTS2.

In another preferred embodiment, the compound is tested in the presence of agents that modulate the hERG gene and/or proteins in the ubiquitin-proteasome pathway.

Another aspect of the invention provides a composition comprising at least one compound which inhibits the ubiquitin-proteasome pathway for use in inducing redirection (re-trafficking) of mutant hERG potassium channel towards the sarcolemma.

According to a further aspect, the invention provides the use of a compound which inhibits the ubiquitin-proteasome pathway for the preparation of a medicament for the prophylaxis or treatment of a disease associated with prolonged ventricular repolarization (cardiac arrhythmia) caused by one or more mutations in the amino acid sequence of the hERG potassium channel.

In a preferred embodiment the disease is hereditary long QT syndrome 2 (LQTS2).

In another preferred embodiment, the at least one compound redirects hERG from the endoplasmic reticulum to the sarcolemma.

The at least one compound is preferably N—[N—(N-Acetyl-L-leucyl)-L-leucyl]-L-norleucine.

Another embodiment of the invention provides a method of prophylaxis or treatment of a disease associated with prolonged ventricular repolarization (cardiac arrhythmia), caused by one or more mutations in the amino acid sequence of the hERG potassium channel, comprising administering to a subject in need of such prophylaxis or treatment an efficacious amount of a compound which redirects (re-trafficks) hERG from the endoplasmic reticulum to the sarcolemma.

BRIEF DESCRIPTION OF THE FIGURES

FIG. 14: Differential hERG distribution in hiPSC-CMs. (A) PCR showing allelic expression of KCNH2 in control and two LQTS2-CMs clones. (B) Pyrogram showing quantitative allelic expression of KCNH2 in control and LQTS2-CMs (left). Summary of allelic variation (C vs T) in control and LQTS2-CMs. (C) Western blots showing hERG levels in LQTS2-CMs, LQTS2-CMs+ALLN and control-CMs. Note the differences in glycosylated vs non-glycosylated hERG protein within the groups. β-actin was used as a loading control. Note that densitometry analysis of hERG shows marked differences in the three groups. Arrowhead on left peak show 155 kDa and arrowhead on right peak show 135 kDa forms of hERG. (D) Immunostaining of CMs against α-actinin (i,iv,vii) and hERG (ii,v,viii) in control (i-iii), LQTS2 (iv-vi) and LQTS2+ALLN (vii-ix) treated CMs with DAPI counterstained nuclei. Arrowhead pointing top left and Arrowhead pointing bottom right (in ii and viii): membrane hERG localization, Arrowhead pointing bottom left (in v): peri-nuclear hERG sequestering. Insets show magnified view of selected segment (boxed) of control (iii), LQTS2 (vi) and LQTS2+ALLN (ix). Scale bar, 50 μm. (E) Membrane intensities plot of hERG in control, LQTS2 and LQTS2+ALLN groups. (F) Summary of membrane mean intensities and peri-nuclear ratio (peri-nuclear area/nuclear area; n=15), respectively. Group 1 (Control) and 2 (LQTS2), n=22, Group 3 (LQTS2+ALLN), n=37). Bars represent mean±SEM. P values indicated by ANOVA.

DEFINITIONS

Figure 1A:
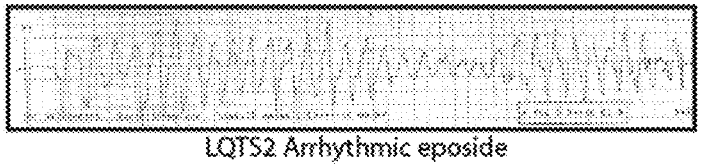
FIG. 1: Clinical Profile of LQTS2 patient. (A) Arrhythmogenic episode of the LQTS2 patient. (B) ECGs from the type-2 LQTS patient during sinus rhythm with QTc of 584 ms. (C) KCNH2 DNA sequencing of patient fibroblast (LQTS2-HFF) shows the C1682T heterozygous missense mutation.

The terms "hERG", "KCNH2" and "$K_v$11.1" may be used interchangeably in the context of the invention. Moreover, the terms "redirects" and "re-traffics" are used interchangeably in the context of the invention.

An "embryoid body" (EB) refers to an aggregate of cells derived from pluripotent cells, where cell aggregation can be initiated by any method that prevents the cells from adhering to a surface to form typical colony growth.

The term "induced pluripotent stem cell" (iPSC) refers to a pluripotent stem cell derived from a non-pluripotent cell (e.g. an adult somatic cell). Induced pluripotent stem cells are identical to embryonic stem cells in the ability to form any adult cell, but are not derived from an embryo.

As used herein, the term "pluripotent" refers to the potential of a stem cell to make any differentiated cell of an organism. Pluripotent stem cells can give rise to any fetal or adult cell type. However, alone they cannot develop into a fetal or adult organism because they lack the potential to contribute to extra-embryonic tissue, such as the placenta.

As used herein, the term "modulates" refers to up-regulation or down regulation of the amount or expression of a substance. The term "up-regulation" refers to a situation where one or more compounds act to increase the expression level of a substance, whether it is a protein or the mRNA encoding the protein, compared to an untreated or control state.

As used herein, the term "modulates single allele of hERG gene" is in the context of the following. The clinical heterozygous mutation of the hERG gene (1 paternal and 1 maternal allele), i.e. 1 allele is normal and another allele is abnormal/mutant is the norm in clinical LQTS2. The disease is only manifesting itself if the mutant allele is expressing highly and/or is dominating over the normal allele. Any agent that is able to suppress the expression or effect of the mutant allele or promote the normal allele will likely restore the hERG function and therefore treat the LQTS2. This is where we believe ALLN, for example (used in this study), exerts its effect, by reducing the burden of the mutant allele by correcting the balance between the expression and/or the effect of the normal vs. mutant allele. This is the first time being shown in any literature that such allelic dominance is only manifesting itself in cardiomyocytes, but not in other unrelated cells in the same patient.

As used herein, the term "mutation" refers to an alteration in the nucleotide sequence of DNA. For example, a missense mutation is when the change of a single base pair causes the substitution of a different amino acid in the resulting protein. This amino acid substitution may have no effect, or it may render the protein nonfunctional. In reference to the A561V missense mutation in the hERG gene, the change in amino acid at position 561 causes incorrect processing and translocation of the channel protein.

As used herein, the term "an", such as used in "an agent" may include within its scope one or more of said agents. For example, an agent that modulates at least one of calpain, calpastatin, and ubiquitin expression encompasses more than one agent when the expression of more than one of calpain, calpastatin and ubiquitin are to be modulated. Further, one or more of said agents may be used to modulate a single protein such as, for example, calpain.

DETAILED DESCRIPTION OF THE INVENTION

The present invention, in one aspect, provides a method for testing compounds for activity in ameliorating an LQTS2 phenotype in a cell or animal, comprising the steps;

(a) contact LQTS2-specific cardiomyocytes or embryoid bodies (EBs) with the compound, and (b) quantitate the level of hERG protein in the endoplasmic reticulum (ER) and in the sarcolemma, and compare the relative level of hERG in the ER and sarcolemma with untreated cardiomyocytes or EBs, wherein an increase in sarcolemma level and a decrease in ER level of hERG in the treated cardiomyocytes or EBs indicates re-trafficking of hERG and the compound has LQTS2-ameliorating activity and/or (c) quantitate the level of glycosylated (mature) hERG protein and compare with untreated cardiomyocytes or EBs, wherein increased glycosylation indicates the compound has LQTS2-ameliorating activity, and/or (d) measure the local field potential duration (FPD), correct for the beating rate of contracting areas (cFPD), and compare with untreated cardiomyocytes or EBs, wherein a time-dependent reduction in cFPD indicates the compound has LQTS2-ameliorating activity, and/or (e) measure the action potential duration (APD), and compare with untreated cardiomyocytes or EBs, wherein a time-dependent reduction in APD indicates the compound has LQTS2-ameliorating activity.

The LQTS2-specific cardiomyocytes and EBs may or may not spontaneously contract or be induced to contract. For example, the cells do not necessarily need to be in a contracting state in order to determine the cellular location of the hERG protein, or the protein's degree of glycosylation.

In a preferred embodiment, the method comprises a further step of culturing the LQTS2-specific cardiomyocytes or EBs until they are spontaneously contracting or induced to contract.

In a preferred embodiment, in step (i) the level of hERG protein is determined by immunostaining.

In another preferred embodiment, in step (ii) the level of glycosylated (mature) hERG protein is determined by western blot.

The FPD may, for example, be measured using a micro-electrode array recording system, and the APD may be measured using whole cell patch-clamp recording methods as described herein.

Another preferred embodiment of the method is directed towards when the phenotype is cardiac rhythm disturbance, comprising the steps;

(a) culture LQTS2-specific cardiomyocytes or embryoid bodies (EBs) until spontaneously contracting or induced to contract, (b) contact the cardiomyocytes or EBs with the test compound, and (i) an agent that triggers arrhythmia and/or (ii) an agent that increases cardiomyocyte or EB beating rate, (c) measure the local field potential duration (FPD), correct for the beating rate of contracting areas (cFPD), and compare with untreated cardiomyocytes or EBs, wherein a time-dependent reduction in cFPD indicates the compound has rhythm normalizing activity, and/or (d) measure the action potential duration (APD), and compare with untreated cardiomyocytes or EBs, wherein a time-dependent reduction in APD indicates the compound has repolarization normalizing activity.

In another preferred embodiment, the method according to the invention comprises the steps;

(a) culture LQTS2-specific cardiomyocytes or embryoid bodies (EBs) until spontaneously contracting or induced to contract, (b) contact the cardiomyocytes or EBs with the test compound, and (i) an agent that modulates single allele of hERG gene in cardiomyocytes or EBs, and/or (ii) an agent that modulates any one or more of calpain, calpastatin, and ubiquitin expression, and/or (iii) an agent that modulates any one or more of HSP70, HSP90 and CAV3 expression, (c) measure the local field potential duration (FPD), correct for the beating rate of contracting areas (cFPD), and compare with untreated cardiomyocytes or EBs, wherein a time-dependent reduction in cFPD indicates the compound has LQTS2-ameliorating activity, and/or (d) measure the action-potential duration (APD), and compare with untreated cardiomyocytes or EBs, wherein a time-dependent reduction in APD indicates the compound has LQTS2-ameliorating activity, and/or (e) measure the hERG channel kinetic and compare with the untreated cardiomyocytes or EBs, wherein a normalizing channel kinetic indicates the compound has LQTS2-ameliorating activity.

In a preferred embodiment of the method, in step (i) the hERG gene modulator is hERG gene-specific siRNA. Small interfering RNA (siRNA), sometimes known as short interfering RNA or silencing RNA, is a class of double-stranded RNA molecules, 20-25 base pairs in length. siRNA can be used to interfere with the expression of specific genes with complementary nucleotide sequence. Any method known in the art suitable for introducing siRNA into the cardiomyocytes or EBs to inhibit activity of a hERG gene allele is intended to fall within the scope of the invention. For example, siRNAs can be introduced by transfection. The publication by Elbashir S M, et al., (*Methods* 2002; 26(2): 199-213), provides suitable methods and is herein incorporated by reference.

In another preferred embodiment of the method, in step (ii) the ubiquitin modulator is selected from the group comprising rapamycin, N—[N—(N-Acetyl-L-leucyl)-L-leucyl]-L-norleucine, PYR-41, MLN4924, SMER3, BAY11-7082 and Nutlin-3.

In another preferred embodiment of the method, in step (ii) the calpastatin modulator is an introduced expression system for calpastatin, such as an introduced plasmid/vector construct that comprises the nucleotide sequence of calpastatin, or the calpastatin is introduced via gene therapy. Any method known in the art suitable for introducing a system for expressing exogenous calpastatin in the cardiomyocytes or EBs is intended to fall within the scope of the invention. Publications such as Molecular Cloning: A Laboratory Manual (Fourth Edition) (Joe Sambrook and Michael Green, Cold Spring Harbor Laboratory Press), and WO 2001032901 A1; WO 2000078119 A2 provide suitable methods and are herein incorporated by reference. Up-regulated expression of calpastatin to suppress calpain activity is a potential way to rescue LQTS2.

In another preferred embodiment of the method, in step (ii) the calpain modulator is selected from the group comprising 4PBA, N—[N—(N-Acetyl-L-leucyl)-L-leucyl]-L-norleucine, MG-132, 3-[6-[[1-(2,2-difluoro-1,3-benzodioxol-5-yl)cyclopropanecarbonyl]amino]-3-methylpyridin-2-yl]benzoic acid, AK275, MDL28170, PD150606, SJA6017, ABT-705253 and SNJ-1945.

In a preferred embodiment of the method, in step (iii) the HSP70 modulator is any one or more selected from the group comprising 2-Phenylethynesulfonamide, Pifithrin-μ, 2,5'-thiodipyrimidines, 5-(phenylthio)pyrimidines, 2-(pyridin-3-ylthio)pyrimidines, 3-(phenylthio)pyridines, MKT-077, rapamycin and VER155008.

In another preferred embodiment of the method, in step (iii) the CAV3 modulator is SB203580.

In another preferred embodiment of the method, in step (iii) the HSP90 modulator is any one or more selected from the group comprising 4-hydroxytamoxifen, tomoxifen, activator of Hsp90 ATPase homolog1 (AHA1).

Another preferred embodiment of the method provides when the phenotype is cardiac rhythm stability, comprising the steps;

(a) culture LQTS2-specific cardiomyocytes or embryoid bodies (EBs) until spontaneously contracting with normal rhythm, (b) contact the cardiomyocytes or EBs with the test compound, and (i) an agent that increases cardiomyocyte or EB beating rate, and/or (ii) an agent that triggers abnormal cardiac rhythm, (c) measure the local field potential duration (FPD), correct for the beating rate of contracting areas (cFPD), and compare with untreated cardiomyocytes or EBs, wherein a time-dependent reduction in cFPD indicates the compound has rhythm normalizing activity, and/or (d) measure the action potential duration (APD), and compare with untreated cardiomyocytes or EBs, wherein a time-dependent reduction in APD indicates the compound has repolarization normalizing activity, and/or (e) measure the presence of early after-depolarizations (EADs) and compare to untreated cardiomyocytes or EBs, wherein the suppression of EADs indicates the compound has arrhythmia suppressing activity.

It is preferred that the agent that increases cardiomyocyte beating rate is any one or more selected from the group comprising isoprenaline, dobutamine, epinephrine, norepinephrine and xamoterol.

It is preferred that the agent that triggers abnormal cardiac rhythm is any one or more selected from the group comprising hERG blocking activity such as E-4031, terfenadine, roxithromycin, fluconazole, cisapride, astemizole.

Another aspect of the invention provides a composition comprising at least one compound which inhibits the ubiquitin-proteasome pathway for use in inducing redirection (re-trafficking) of mutant hERG potassium channel towards the sarcolemma.

According to a further aspect, the invention provides the use of a compound which inhibits the ubiquitin-proteasome pathway for the preparation of a medicament for the prophylaxis or treatment of a disease associated with prolonged ventricular repolarization (cardiac arrhythmia) caused by one or more missense mutations in the amino acid sequence of the hERG potassium channel.

In a preferred embodiment the disease is hereditary long QT syndrome 2 (LQTS2).

In another preferred embodiment, the at least one compound redirects hERG towards the sarcolemma, reduces repolarization, increases $I_{Kr}$ currents and/or reduces arrhythmogenic events.

Another embodiment of the invention provides a method of prophylaxis or treatment of a disease associated with prolonged ventricular repolarization (cardiac arrhythmia), caused by one or more mutations in the amino acid sequence of the hERG potassium channel, comprising administering to a subject in need of such prophylaxis or treatment an efficacious amount of a compound which redirects (re-trafficks) hERG from the endoplasmic reticulum to the sarcolemma.

In accordance with the various embodiments of the invention described supra, the at least one compound is preferably an ubiquitin-proteasome inhibitor.

Preferably, the compound is any one or more selected from the group comprising N—[N—(N-Acetyl-L-leucyl)-L-leucyl]-L-norleucine (ALLN); 3-[6-[[1-(2,2-difluoro-1,3-benzodioxol-5-yl)cyclopropanecarbonyl]amino]-3-methylpyridin-2-yl]benzoic acid (VX-809). More preferably the compound is N—[N—(N-Acetyl-L-leucyl)-L-leucyl]-L-norleucine.

LQTS2-specific cardiomyocytes (A561V missense mutation in KCNH2) were generated from induced pluripotent stem cells using virus-free reprogramming method. These cardiomyocytes recapitulate dysfunction of hERG potassium channel with diminished $I_{Kr}$ currents, prolonged repolarization durations and elevated arrhythmogenesis due to reduced membrane localization of glycosylated/mature hERG. Dysregulated expression of folding chaperones and processing proteasomes coupled with sequestered hERG in the endoplasmic reticulum confirmed trafficking-induced disease manifestation. Treatment with ALLN (N—[N—(N-Acetyl-L-leucyl)-L-leucyl]-L-norleucine), not only increased membrane localization of mature hERG but also reduced repolarization, increased $I_{Kr}$ currents and reduced arrhythmogenic events. Diverged from biophysical interference of hERG channel, our results show that modulation of chaperones proteins could be therapeutic in LQTS2 treatment.

This in vitro study shows an alternative approach to rescue diseased LQTS2 phenotype via corrective re-trafficking therapy using a small chemical molecule such as ALLN. This approach may have ramifications in other clinically relevant trafficking disorders. The methods of the invention allow the testing of compounds on LQTS2-specific cardiomyocytes or EBs, for their ability to effect normalization of various aspects of the LQTS2 phenotype, via the ubiquitin-proteasome pathway.

Having now generally described the invention, the same will be more readily understood through reference to the following examples which are provided by way of illustration, and are not intended to be limiting of the present invention.

EXAMPLES

Generation of Human iPSCs.

Reprogramming of patient-derived skin fibroblasts was performed with episomal plasmids as reported previously. Briefly, the patient-derived skin fibroblasts were co-transfected with two oriP/EBNA1-based episomal plasmids (EO2S CK2M EN2L, pEP4 EO2S ET2K from Addgene Inc, MA, USA) via nucleofection (NHDF-VPD-1001 with U-20 program, Amaxa, Walkersville, Md.) was performed. Transfected fibroblasts ($1.0\times10^6$ cells per nucleofection) were directly plated to 10-cm mitomycin-C inactivated MEF-seeded dishes with fibroblast culture medium. Culture medium was exchanged every other day. On day 4 post-transfection, the foreskin fibroblast culture medium was replaced with human ES cell culture medium (Mehta A, et al., 2008; Mehta A, et al., 2010) with 100 ng/ml of bFGF (R and D Systems, USA). Colonies with morphology similar to hESC colonies were readily visible between day 21-25 post-transfection. Individual colonies were picked manually and plated on 1% matrigel coated dishes and maintained in mTeSR1 medium (Stem Cell Technologies, VA, Canada). Enzymatic passaging with 1 mg/ml dispase was employed for expansion, characterization and differentiation (Mehta A, et al., 2011).

Embryoid Body Formation and Cardiomyocyte Differentiation.

Pluripotent stem cell colonies were dispersed into small clumps with dispase (1 mg/ml) and, placed in low adhesion culture dishes in EB medium (Mehta A, et al., 2010) along with or without 5 μM of SB203580 (Calbiochem, USA) for 8 days (Mehta A, et al., 2011). Subsequently, EBs were plated on 0.1% gelatin-coated dishes in EB media without SB203580. Beating areas were typically observed around day 11-14 from EB formation. Beating areas were manually cut after day 21 of differentiation and utilized for experiments.

Immunfluorescence.

Colonies of iPSC and single cells generated from beating clusters were seeded on matrigel- and gelatin-coated glass slides respectively. Both cell types were fixed with 4% paraformaldehyde, permeabilized with 1% Triton X-100 (Sigma-Alrich, MO, USA) and blocked with 5% bovine serum albumin (Sigma-Alrich, MO, USA). Human iPS colonies were stained for 1 hour with primary antibodies targeting pluripotency markers, Oct-4, SSEA4, Tra-1-60 and Tra-1-80 (all Millipore, MA, USA), whereas cardiomyocytes (CMs) were stained with primary antibodies, α-actinin (Sigma-Alrich, MO, USA), MLC (USBiologicals, MA, USA), titin (DHSB, Iowa, USA), SERCA (Sigma-Alrich, MO, USA), hERG (Abcam, MA, USA) and calpastatin (Millipore, MA, USA). Samples were washed and incubated with respective secondary antibodies (Invitrogen, CA, USA) for 1 hour and subsequently counterstained with DAPI. Slides were examined under Zeiss LSM710 NLO multi-photon confocal microscope (Carl Zeiss Inc, USA).

All human studies performed conform to the declaration of Helsinki and all experimental protocols and studies were approved by the Institutional Review Board (IRB) of the host institute.

Teratoma Formation

Animal experiments were conducted following experimental protocols approved by the Institutional Ethics Committee on Experimental Animals, in full compliance with Singapore laws and regulations and followed the guidelines by US National Institutes of Health Guide for the Care and Use of Laboratory Animals. SCID mice, 6-week old, weighing 20-23 g, were obtained from SingHealth Experimental Medicine Centre and were anesthetized with 2% isofluorane initially followed by 1% isofluorane during surgery. Approximately $1\times10^6$ hiPS cells, were injected into the kidney capsule as previously described. Mice were euthanized with carbon dioxide asphyxiation at 8-week after injections and tumors collected, fixed and processed for standard H&E staining.

Karyotype Analysis.

Karyotype analysis was performed using standard G-banding chromosome analysis by the K.K. Hospital's cytogenetic laboratory (Singapore) according to standard procedures.

DNA Sequencing.

Genomic DNA was isolated from the patient fibroblasts, patient- and control-hiPSCs using QIAamp DNA kit (Qiagen GmbH, Hilden, Germany). The relevant DNA fragment of the KCNH2 gene was amplified by PCR reaction using 100 ng genomic DNA (primer sequences in Table 1) and the PCR products were sequenced.

TABLE 1

| SEQ ID NO. | Gene name | Forward primer | SEQ ID NO. | Reverse primer |
|---|---|---|---|---|
| 1 | KCNH2 (Seq) | ATGACGCAGATGGAGAAGA | | — |

TABLE 1-continued

| SEQ ID NO. | Gene name | Forward primer | SEQ ID NO. | Reverse primer |
|---|---|---|---|---|
| 2 | KCNH2 (RE) | CTGATCGGGCTGCTGAAGAC | 3 | AGCCAATGAGCATGACGCA |
| 4 | KCNH2 (AS)-Wt | TGCACCTTTGCGCTCATCCC | 5 | GCGCCGTCACATACTTGTCCTTG |
| 6 | KCNH2 (AS)-Mt | TGCACCTTTGCGCTCATCCT | 7 | GCGCCGTCACATACTTGTCCTTG |
| 8 | KCNH2 (AS)-Total | CGTGCTGCCTGAGTACAAGCT | 9 | TGTGAAGACAGCCGTGTAGATGA |
| 10 | GAPDH | GTGGACCTGACCTGCCGTCT | 11 | GGAGGAGTGGGTGTCGCTGT |
| 12 | Oct-4 | AGTTTGTGCCAGGGTTTTTG | 13 | ACTTCACCTTCCCTCCAACC |
| 14 | Sox-2 | AAAAATCCCATCACCCACAG | 15 | GCGGTTTTTGCGTGAGTGT |
| 16 | Nanog | CTCCATGAACATGCAACCTG | 17 | GAGGAAGGATTCAGCCAGTG |
| 18 | hTert | TGGCAGGTGTACGGCTTCGT | 19 | CAGCTCCTGCAGCGAGAGCT |
| 20 | Nestin | CAGGAGAAACAGGGCCTACA | 21 | TAAGAAAGGCTGGCACAGGT |
| 22 | Pax 6 | CCGGCAGAAGATTGTAGAGC | 23 | CTAGCCAGGTTGCGAAGAAC |
| 24 | AFP | CCGAACTTTCCAAGCCATAA | 25 | TGGCATTCAAGAGGGTTTTC |
| 26 | HNF4 α | CAGGCTCAAGAAATGCTTCC | 27 | GTGCCGAGGGACAATGTAGT |
| 28 | Isl11 | AAGGACAAGAAGAGAAGCAT | 29 | CATGGGAGTTCCTGTCATCC |
| 30 | GATA4 | TCCAAACCAGAAAACGGAAG | 31 | AAGGCTCTCACTGCCTGAAG |
| 32 | Nkx2.5 | CTAAACCTGGAACAGCAGCA | 33 | GTAGGCCTCTGGCTTGAAGG |
| 34 | cTnl | CCAACTACCGCGCTTATGC | 35 | CTCGCTCCAGCTCTTGCTTT |
| 36 | MLC2v | CCTTGGGCGAGTGAACGT | 37 | GGGTCCGCTCCCTTAAGTTT |
| 38 | MYH7 | GGCAAGACAGTGACCGTGAAG | 39 | CGTAGCGATCCTTGAGGTTGTA |
| 40 | CACNA1D | GGGCAATGGGACCTCATAAATAA | 41 | TTACCTGGTTGCGAGTGCATTA |
| 42 | HCN4 | GACCGCATTGGCAAGAAGAAC | 43 | GGGCCATCTCCCGGTCAT |
| 44 | CAPN1 | CCAAGCAGGTGAACTACCGA | 45 | GGTCCACGTTGTTCCACTCT |
| 46 | CAPN2 | GCAGGAACTACCCGAACACA | 47 | TGCTTCTGAATGAGCCCCAC |
| 48 | CAPN3 | GTCAACGACGCAGGATTCCA | 49 | GAACATGCCCTCCAGCCTAA |
| 50 | CAST | CTGCAATATCTGGCAAGCCG | 51 | ATCCATGCCTGACTTTCCCG |
| 52 | CAV3 | CTTTGACGGCGTGTGGAAGGT | 53 | ACCGCCCAGATGTGGCAGA |
| 54 | HSP70 | GGTATAAGAGGCAGGGTGGC | 55 | GACATGGTTGCTGGGGTGTA |
| 56 | HSP90 | ATGATTGGCCAGTTCGGTGT | 57 | GGTTCACCTGTGTCTGTCCT |
| 58 | UBB | ATTTAGGGGCGGTTGGCTTT | 59 | TGCATTTTGACCTGTTAGCGG |
| | | Genomic | | |
| 60 | Oct-4 | AGTGAGAGGCAACCTGGAGA | 61 | AGGAACTGCTTCCTTCACGA |
| 62 | Nanog | CAGAAGGCCTCAGCACCTAC | 63 | AGGAACTGCTTCCTTCACGA |
| 64 | c-Myc | TCAAGAGGCGAACACACAAC | 65 | AGGAACTGCTTCCTTCACGA |
| 66 | Sox-2 | ACCAGCTCGCAGACCTACAT | 67 | CCCCCTGAACCTGAAACATA |
| 68 | KLF4 | CCCACACAGGTGAGAAACCT | 69 | CCCCCTGAACCTGAAACATA |
| 70 | EBNA-1 | ATCGTCAAAGCTGCACACAG | 71 | CCCAGGAGTCCCAGTAGTCA |

Abbreviations: KCNH2: potassium voltage-gated channel subfamily H member 2; Oct-4: Octamer-4; SOX2: SRY (sex determining region Y)-box 2; Nanog: Nanog homeobox; Nestin: Nestin; Pax 6: paired box 6; AFP: alpha-fetoprotein; HNF4a: hepatocyte nuclear factor 4, alpha; Isl1: Islet-1; GATA4: GATA binding protein 4; NKX2.5: NK2 transcription factor related, locus 5 (*Drosophila*); cTnI: cardiac troponins I; MLC2v: Myosin light chain 2, ventricular; MYH7: Myosin heavy chain 7; CACNA1D: voltage-gated calcium channel alpha subunit Cav1.3; HCN4: hyperpolarization activated cyclic nucleotide-gated potassium channel 4; GADPH: glyceraldehyde-3-phosphate dehydrogenase; CAPN1/2/3: calpain 1/2/3; CAST: calpastatin; CAV3: caveolin-3; HSP70/90: heat shock protein 70/90; UBB: ubiquitin B; c-Myc: myelocytomatosis viral oncogene homolog; KLF-4: Kruppel-like factor 4; EBNA1: Epstein-Barr virus nuclear antigen 1.

Real-Time PCR.

For real-time reverse-transcription polymerase chain reaction (qRT-PCR) analysis, RNA was isolated with the RNeasy kit (Qiagen GmbH, Hilden, Germany). One μg of total RNA was converted to complementary DNA by Superscript III first-strand synthesis system (Invitrogen, CA, USA). cDNA template (5 ng) was used from each sample and SYBR green real-time PCR studies were performed using Quantifast kit (Qiagen GmbH, Hilden, Germany) and primer (Supplementary table 1) as per the kit instructions. Samples were cycled with RotorGene Q (Qiagen GmbH, Hilden, Germany) as follows: 5 minutes at 95° C., followed by 40 cycles of 10 seconds at 95° C. and 30 second extension at 60° C. All experiments were performed in triplicates. Relative quantification was calculated according to the ΔΔCt method for quantitative real-time PCR (using an endogenous control gene, GAPDH). For each gene, the expression at a specific day was then normalized by its baseline values. For genomic DNA PCR, genomic DNA was extracted using QIAamp DNA kit (Qiagen GmbH, Hilden, Germany) as per the manufacturer's instructions. One hundred nanograms genomic DNA was used for PCR and 30 cycles of 95° C. for 15 sec, 60° C. for 30 sec and 72° C. for 30 sec, with initial deactivation at 95° C. for 5 min and final extension at 72° C. for 7 min was performed in GeneAmp PCR system 2700 (Applied Biosystems, USA). PCR products were electrophoresed in 1.5% agarose gel with ethidium bromide (Sigma-Alrich, MO, USA) and bands were visualized and recorded using Geldoc XR (Bio-Rad, USA).

Restriction Enzyme Digestion

PCR amplification for KCNH2 gene was performed as mentioned above from cDNA and the product was cleaned using Qiagen PCR clean-up kit (Qiagen GmbH, Hilden, Germany) and overnight digestion with ApaL1 (Fermentas, USA) performed as per manufacturer's instruction. The digested PCR products were electrophoresed in 3% agarose gel with ethidium bromide (Sigma-Alrich, MO, USA) and bands were visualized and recorded using Geldoc XR (Bio-Rad, USA).

Pyrosequencing

Pyrosequencing was performed using PSQ 96HS system (Qiagen GmbH, Hilden, Germany) by EpigenDX (EpigenDX Inc, MA, USA), and analysis was performed as per manufacturer's recommended protocol.

Western Blots and Co-Immunoprecipitation (IP)

Contracting cardiomyocyte clusters from all groups were collected and lysed in RIPA buffer (Thermo Scientific, USA). Protein concentration was estimated using Pierce BCA protein Assay kit as per the manufacturer's instruction (Thermo Scientific, USA). Equal amounts of protein (15 μg) were loaded on a gradient 4-12% Bis-Tris NuPage Gel (Life Technologies, USA) and run at 200V for 35 min and dry transferred to nitrocellulose (NC) membrane using iBlot (Life Technologies, USA) as per manufacturer's instruction. NC membranes were blocked with 5% BSA for 1 hour and probed overnight with respective primary antibodies, mouse monoclonal anti-Hsp70 (1:5000; Abcam, USA), mouse monoclonal anti-Hsp90 (1:1000; Abcam, USA), calpastatin (1:500; Millipore, MA, USA), rabbit polyclonal Anti-hERG (1:200; Abcam, USA), mouse monoclonal Anti-cardiac troponin T (1:5000; US Biologicals, USA), mouse monoclonal Anti-β-actin (1:10000; Abcam, USA), mouse monoclonal anti-Calpain 3 (1:500; Abcam, USA). Post-probing, the NC membranes were washed with 0.1% PBST (Phosphate buffered saline with tween 20) and NC membranes were probed with respective mouse or rabbit secondary antibody conjugated with HRP (Amersham, USA) for 1 hour. Membranes were washed with PBST and developed using Amersham ECL kit (Amersham, USA) as per manufacturers' instruction. Images were captured using CCD camera. Denstitometric analysis was performed using ImageJ software and values were normalized with loading control (β-actin). Data presented is a mean of 3 independent experiments.

Co-Immunoprecipitation was performed using Dynabead Co-IP kit (Life Technologies, USA) as per the manufacturers' instructions. Briefly, Dynabeads were conjugated with hERG antibody overnight, washed and incubated with cell lysate for 1 h and subsequently hERG protein complexes were eluted. This complex was run on conventional 4-12% Bis-Tris NuPage Gel (Life Technologies, USA), transferred on NC membrane, blocked and immunoblotted (IB) with hsp70 antibody followed by secondary conjugated HRP antibody. The membranes were developed using Amersham ECL kit as per manufacturers' instruction. Images were captured using C-digit blot-scanner (LI-COR, USA).

Live Labelling of CMs with Smartflare™ RNA Probes

Single CMs were plated on 0.1% gelatin coated dishes in normal EB2 medium and incubated overnight with MLC2v Smartflare™ RNA probes at per the manufacturer's instruction (Merk Millipore, USA). Next day, cells were washed with PBS to remove excess of the probes and replaced with fresh EB2 medium. Slides were examined under Fluorescence microscope.

Contracting cells that were Cy3 positive were considered to be MLC2v positive (Ventricular) and other contracting cells were considered to be a mixture of atrial and nodal populations. These ventricular cells were used for patch clamp studies.

Microelectrode Array (MEA) Recordings

To characterize the electrophysiological properties of the hiPS-CMs, a microelectrode array (MEA) recording system (Multichannel Systems, Reutlingen, Germany) was used as described previously. Briefly, contracting areas were microdissected and plated on MEA plates, allowed to adjust for 72 hrs before recording. All clusters were monitored for their beating abilities (beats/min) under the microscope during the 72 hr period. Clusters that maintained relatively uniform beating rates were then subjected to drugs. The MEA system allows simultaneous recordings from 60 titanium nitride-coated gold electrodes (30 μm) at high spatial (200 μm) and temporal (15 kHz) resolutions. All stock drugs were diluted in medium (2 mL) to assess the effects on the electrophysiological properties. The stock drugs were diluted in medium (2 mL). MEA clip along with the beating clusters was maintained on 37° C. throughout the duration of experiments. Care was also taken that all buffers including the medium utilized during all experimentation were prewarmed to 37° C. All tested drugs were procured from Sigma-Aldrich, MO, USA. All extracellular recordings were performed for 180 seconds at baseline and at 5 minutes after drug application at 37° C. Data were recorded using MC Rack software (Multichannel System) and the recordings were used to determine the local field potential duration (FPD). FPD measurements were normalized (corrected FPD [cFPD]) to the beating rate of the contracting areas with the Bazzet correction formula: cFPD=FPD/√(RR interval).

Whole Cell Patch-Clamp Recordings

Spontaneously contracting embryoid bodies were enzymatically dissociated into single cells with 1 mg/ml collagenase IV and attached on glass bottom dishes. Action potentials were recorded in the current clamp mode, and triggered with just-threshold 4 ms current steps at a stimulation rate of 1 Hz until a steady-state was reached with external buffer at 37° C. The external solution contained 138 mM NaCl; 4 mM KCl; 1 mM $MgCl_2$; 2 mM $CaCl_2$; 0.33 mM $NaH2PO_4$; 10 mM glucose, and 10 mM HEPES (pH 7.4 with NaOH). The pipette solution consisted of 120 mM potassium glutamate; 25 mM KCl; 1 mM $MgCl_2$; 1 mM $CaCl_2$ and 10 mM HEPES (pH 7.4 with KOH). Whole patch clamp recording were performed with an Axopatch 700B amplifier (Axon Instrument, Foster City, Calif., USA). Data was acquired and analyzed using pClamp software (Version 10.0; Axon Instrument). For voltage-clamp studies of $I_{Kr}$, the external solution contained 132 mM NaCl; 4 mM KCl; 1.8 mM $CaCl_2$; 1.2 mM $MgCl_2$; 5 mM glucose, and 10 mM HEPES (pH 7.4 with NaOH). The pipette solution contained 140 mM KCl; 4 mM Mg-ATP; 1 mM $MgCl_2$; 5 mM EGTA, and 10 mM HEPES (pH 7.2 with KOH). Nimodipine (1 mM) was added to the external solution to block the L-type $Ca^{2+}$ current. $Na^+$ and T-type $Ca^{2+}$ currents were inactivated by holding potential of −40 mV. $I_{Kr}$ was defined as the E-4031-sensitive (1 μM) current. The holding potential was at −40 mV to +50 mV in 10 mV increments, lasting 5 seconds. Tail current was recorded after the test potential was backed to −40 mV.

Statistical Analysis.

Results were reported as mean±standard error of mean (SEM). Comparison between LQTS2 hiPSC-CMs and healthy control hiPSC-CMs groups was performed using the Student's t-test. One-way ANOVA followed by Tukey's post-hoc tests were used when comparing multiple groups. $p<0.05$ was considered statistically significant.

Results

Generation and Characterization of LQTS2 hiPSC

Figure 1B:
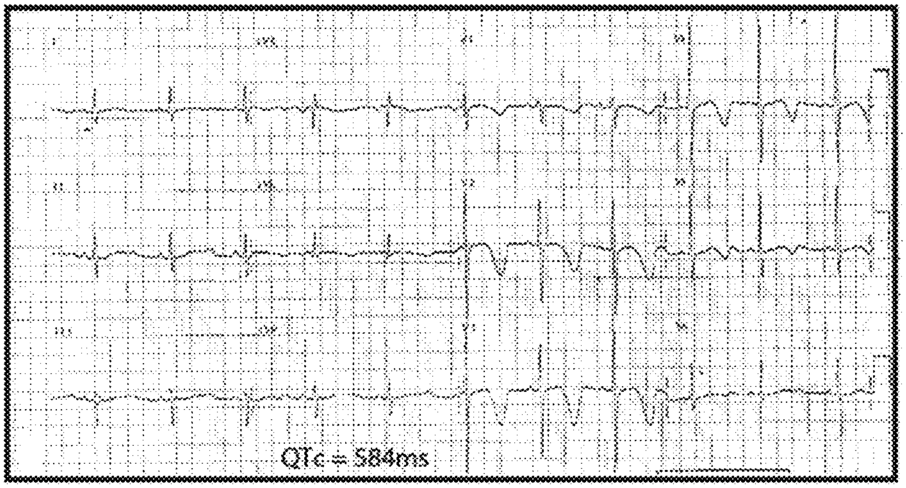
Figure 1C:
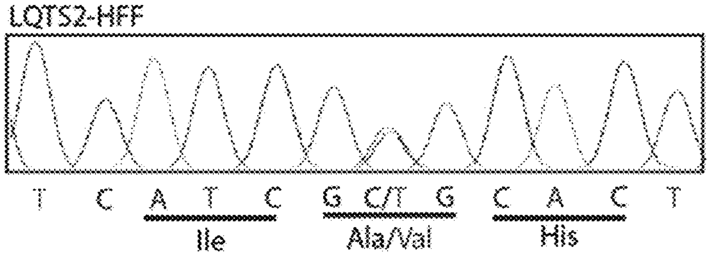
Figure 2A:
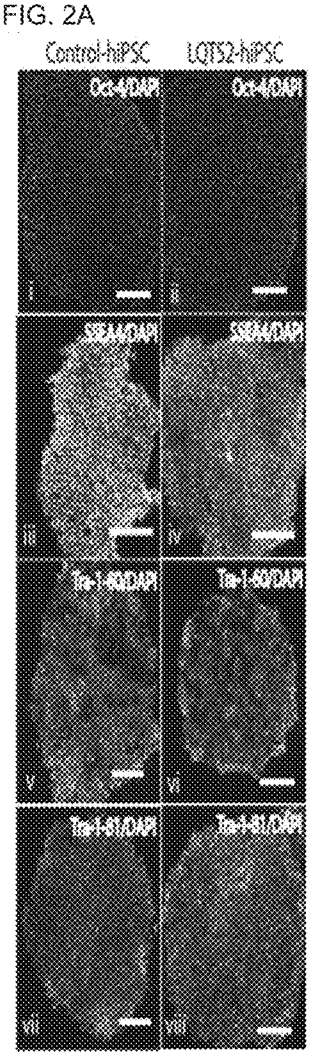
FIG. 2: Characterization of LQTS2-hiPSC. (A) Immunostaining for pluripotency markers in control- and LQTS2-hiPSCs. Scale bars, 200 μm. (B) Karyotyping of LQTS2-hiPSCs. (C) KCNH2 DNA sequencing showing C1682T mutation in LQTS2-ihPSC, absent in control-hiPSC. (D) H&E stained sections show presence of the three germ layers, identified by arrows, in teratoma assay following injection of LQTS2-hiPSCs in NOD/SCID mice. Scale bars, 100 μm. (E) Immunostaining of LQTS2-CMs for α-actinin and MLC (top), titin (middle) and SERCA2a (below) and counterstained with DAPI. Scale bar, 50 μm.
Figure 2B:
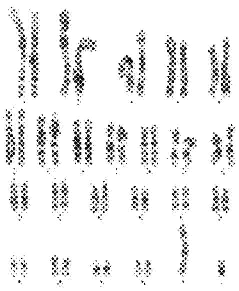
Figure 2C:
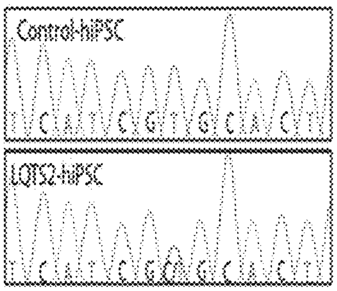
Figure 2D:
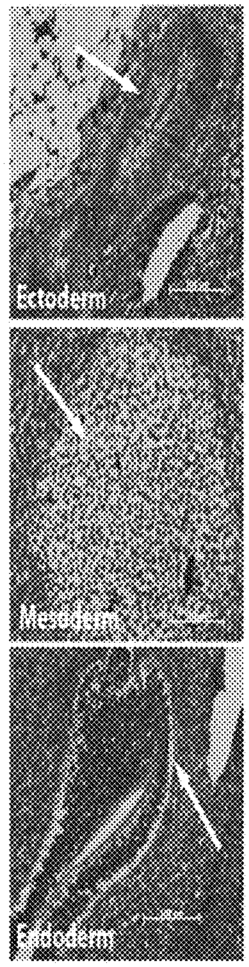
Figure 3:
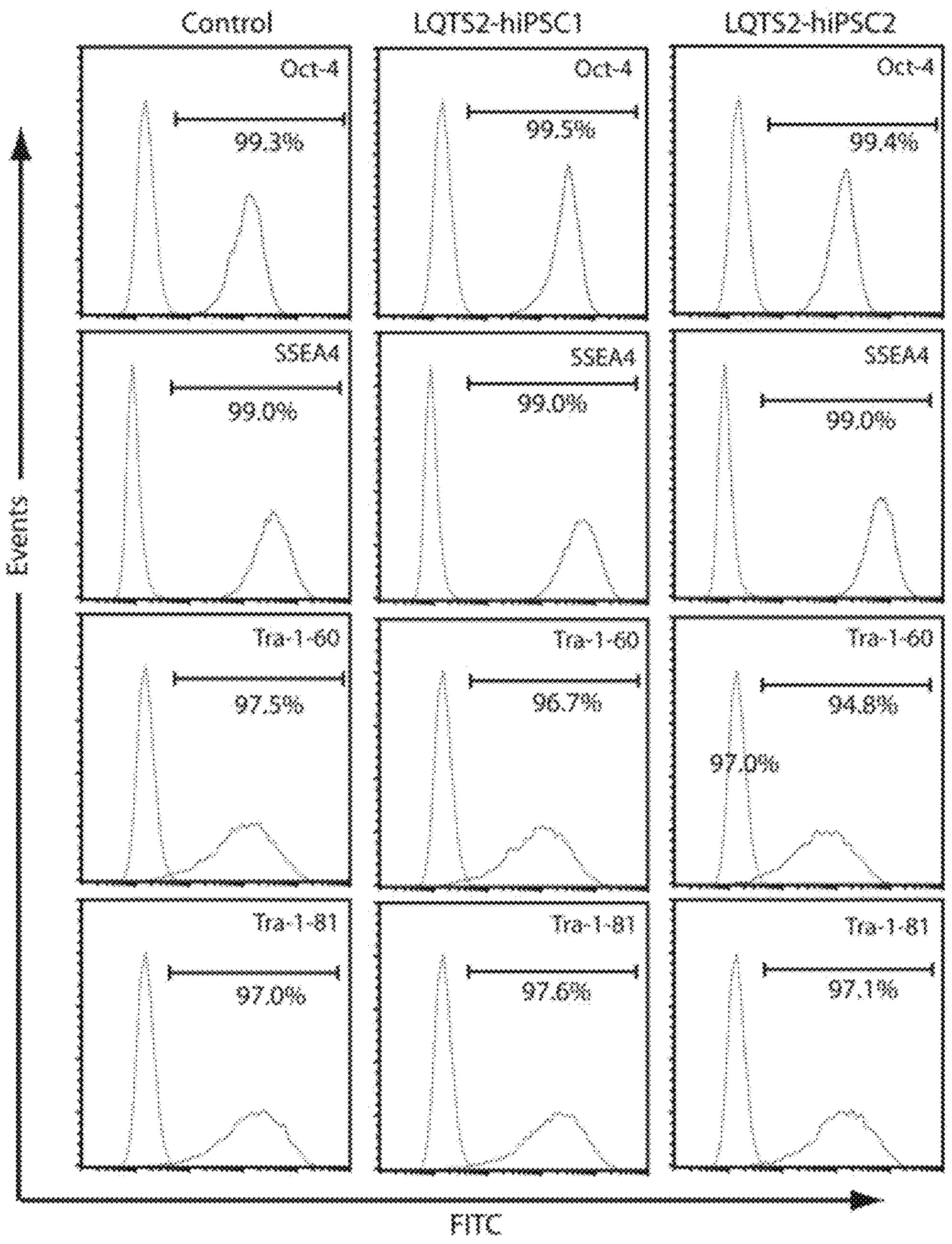
FIG. 3: Flow cytometric analysis of hiPSCs. Flow cytometric analysis of pluripotency markers (OCT4, SSEA4, TRA-1-60 and TRA-1-81) in control- and LQTS2-derived hiPSCs. A total number of 10,000 events were collected for each analysis.
Figure 4:
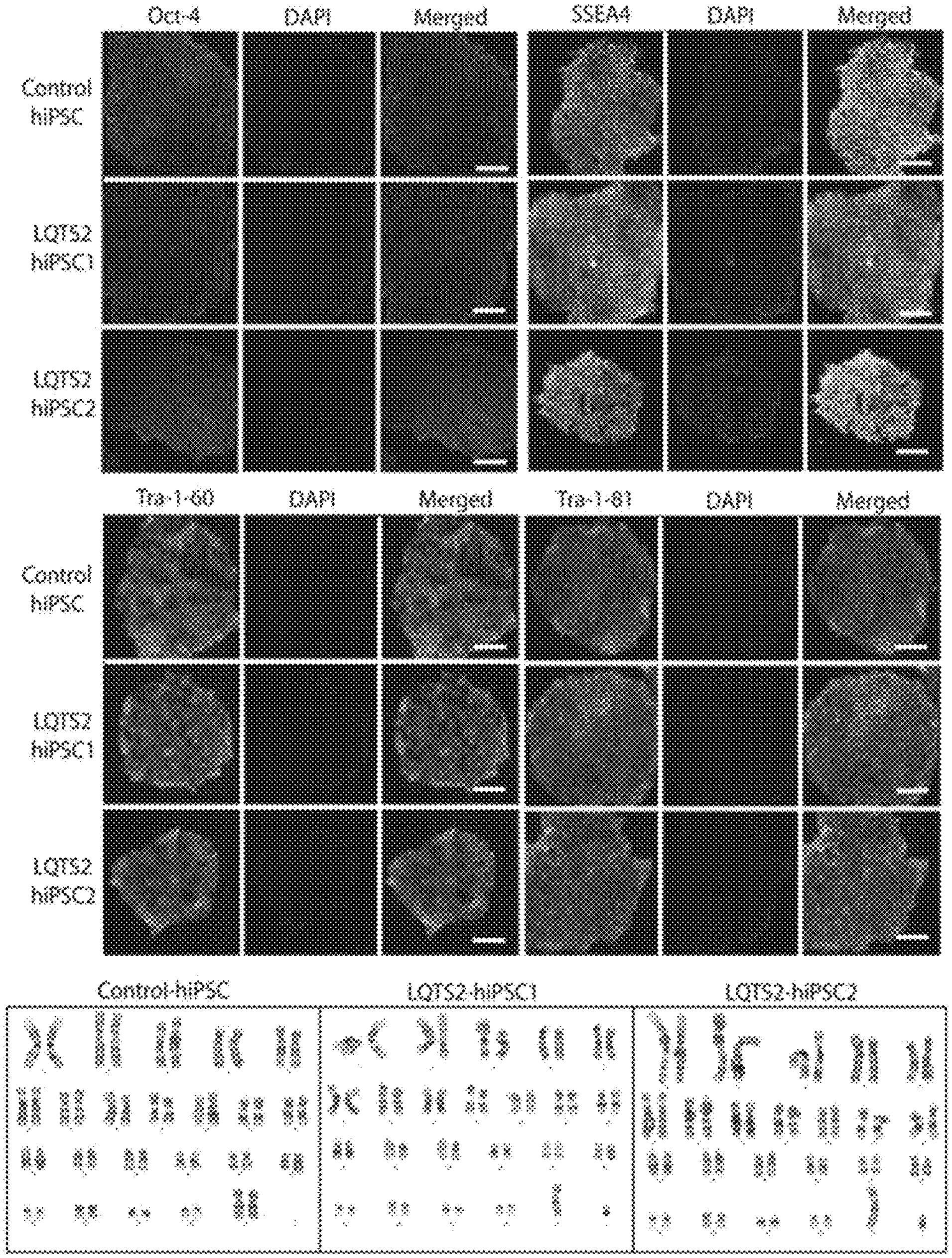
FIG. 4: Immunostaining of undifferentiated hiPSC clones for pluripotency markers. Immunofluorescence staining showing expression of the pluripotency markers OCT4, SSEA4, TRA-1-60 and TRA 1-81 in the normal healthy control-hiPSCs and two different LQTS2-hiPSC clones. Scale bars 200 μm. Bottom panel, karyotype analysis of the control and two LQTS2hiPSC lines.
Figure 5A:
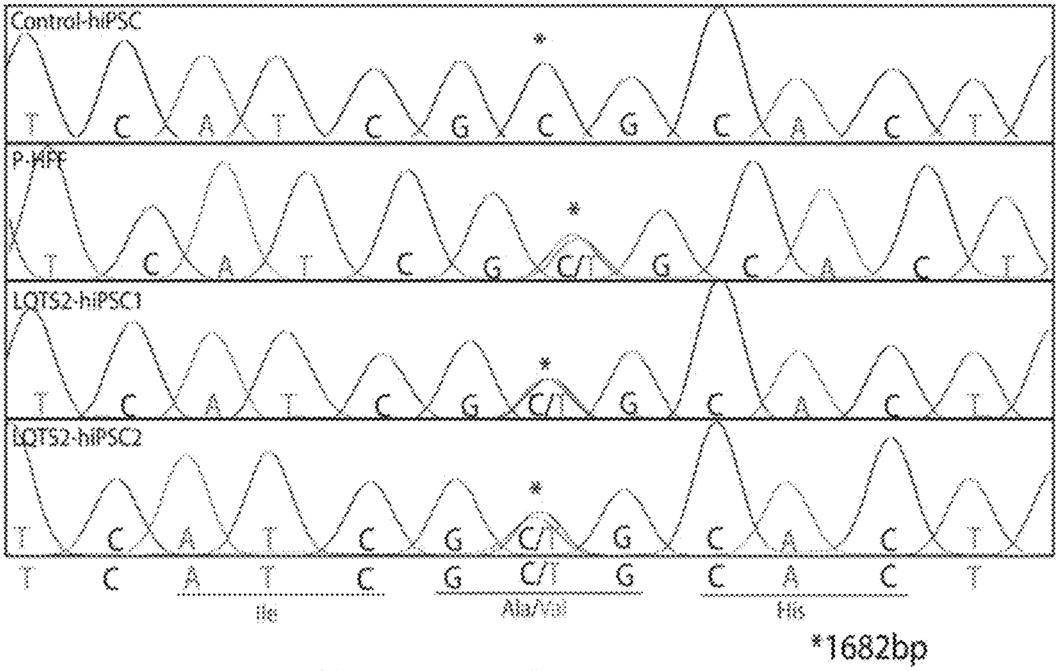
FIG. 5: Mutation characterization of LQTS2-hiPSCs. (a) DNA sequencing of control-hiPSC, Patient fibroblast (P-HFF) and patient-derived two hiPSC clones (LQTS2-hiPSC1/hiPSC2). Note the presence of mutation (C1682T) in patient fibroblasts and two derived hiPSC lines. (b) Restriction digestion of a RT-PCR amplified KCNH2 region with ApaL1. The presence of 264 bp band in LQTS2 demonstrates an incorporation of an additional ApaL1 site due to the mutation as compared to control (Lane 1).
Figure 5B:
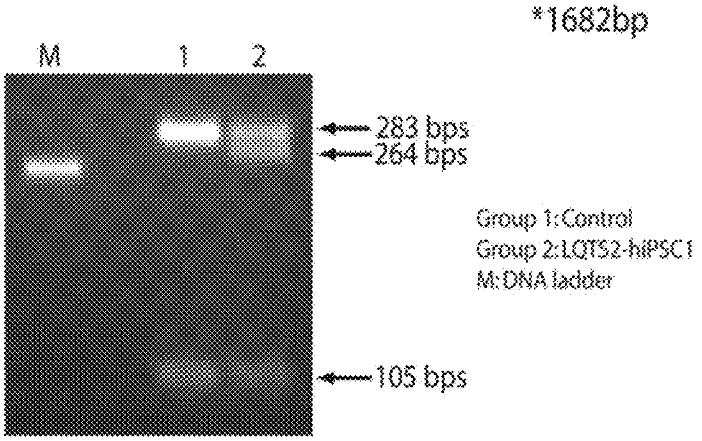
Figure 6A:
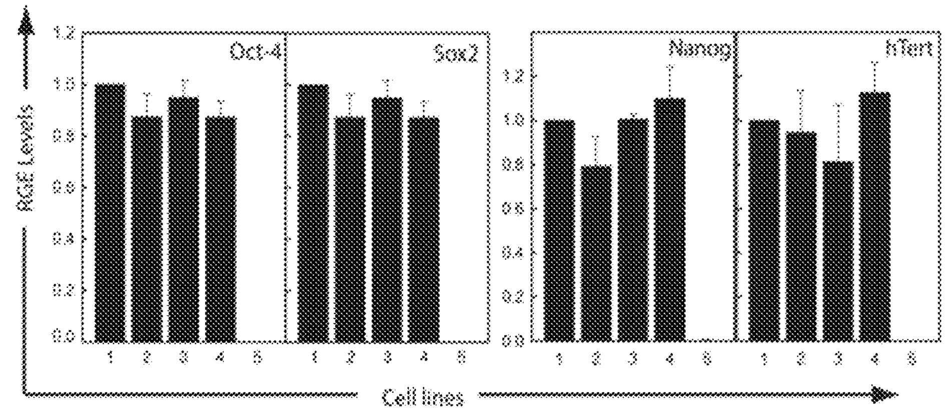
FIG. 6: Quantitative gene expression and genomic integrations. (a) Quantitative RT-PCR analysis of pluripotency marker (OCT4, SOX2, NANOG, HTERT) in control-, LQTS2-derived hiPSCs and patient dermal fibroblasts. Relative gene expression levels were calculated using a standard human embryonic stem cell line, H9. Bars represent mean and SEM. (n=9). No statistical difference was noted between groups (1-4), except group 5 ($p<0.05$). (b) Genomic PCR of control-, LQTS2-derived hiPSCs and patient dermal fibroblasts show no genomic integration of transgene sequences. Positive control is the plasmid used for reprogramming.
Figure 6B:
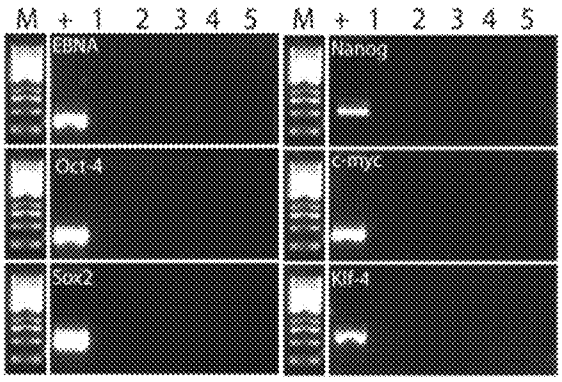
Figure 7:
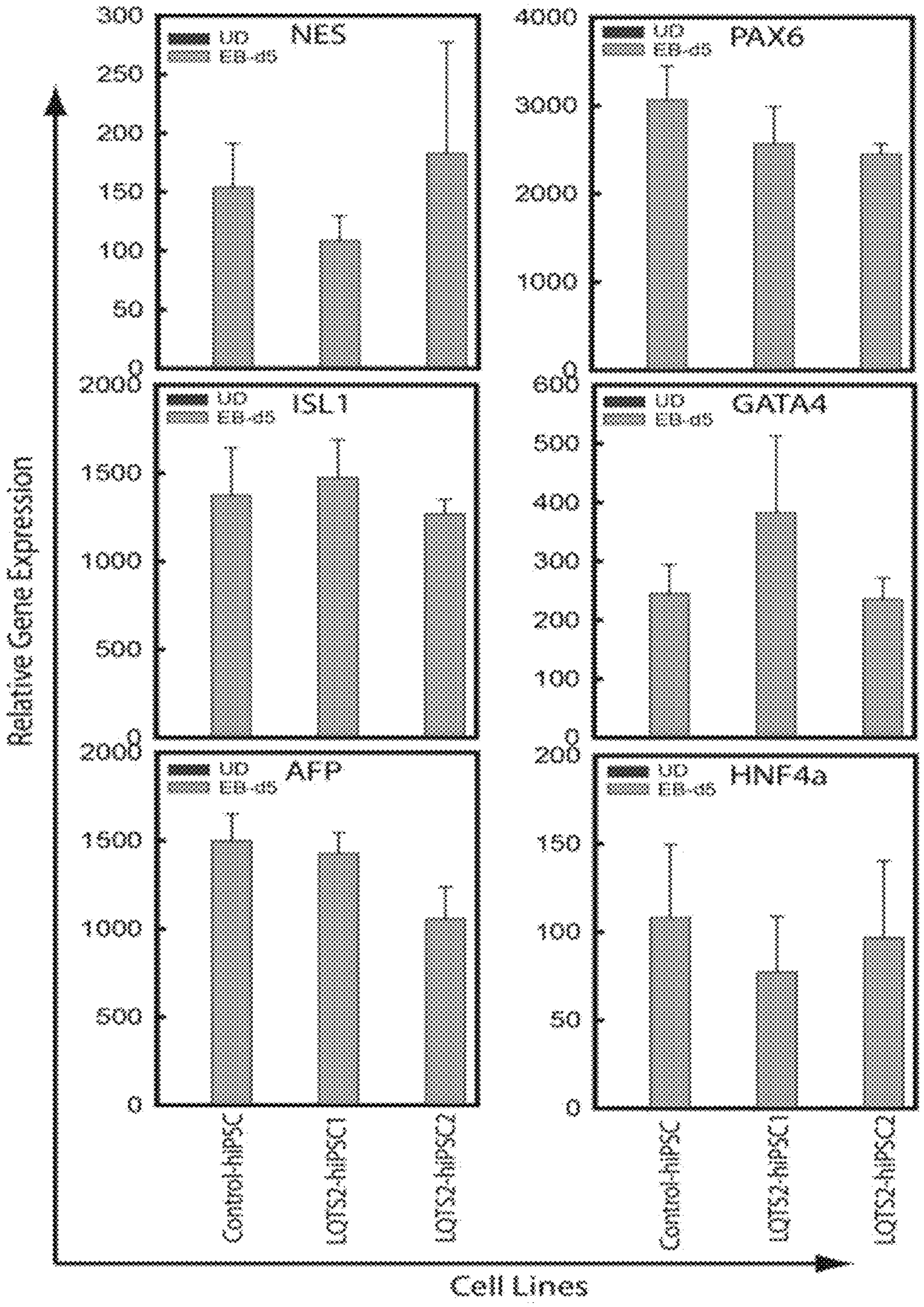
FIG. 7: Real-time gene expression for three germ layers. Real-time RT-PCR analysis of markers indicative of three germ formation, ectoderm (NES, PAX6), mesoderm (ISL1, GATA4) and endoderm (AFP, HNF4a) following differentiation of control- and LQTS2-hiPSCs for 5 days as embryoid bodies. Bars represent mean and SEM (n=9).

Dermal fibroblasts were collected from a 13-year old male (only child of the family), who presented clinical episode of polymorphic ventricular tachycardia (FIG. 1A) with a QTc of 584 ms (FIG. 1B). The patient is currently managed with a beta-blocker (atenolol) and an implantable defibrillator. Genetic screening showed that patient fibroblast exhibited a C1682T heterozygous missense mutation in KCNH2 resulting in an A561V substitution in the S5 transmembrane domain (FIG. 1C). We generated two viral-free LQTS2-hiPSC lines that showed visual morphologies similar to hESC colonies (compact colonies, high nucleus-to-cytoplasm ratios, and prominent nucleoli). Fibroblasts from healthy individuals were used to generate normal control iPSC lines (Mehta A, et al., *Cardiovascular research* 2011; 91:577-586). Immunostaining and flow cytometric analysis for control and LQTS2-hiPSCs showed expression of hallmark pluripotency markers, OCT4, SSEA4, TRA-1-60 and TRA-1-81 (FIG. 2A) in over 95% of the cells with normal karyotype (FIG. 2B; FIGS. 3-4). Genetic screening of the generated LQTS2-hiPSC also exhibited a C1682T heterozygous missense mutation, which was absent in control hiPSC lines (FIG. 2C; FIG. 5). These hiPSCs also demonstrated high levels of pluripotency transcripts, showed no genetic integration of episomal vectors (FIG. 6), were able to form teratomas with cell derivatives of three germ layers following injection in SCID mice (FIG. 2D) and expressed characteristic ecto/meso/endodermal genes via spontaneously differentiated embryoid body (EB) in vitro (FIG. 7).

Cardiac Characterization and Electrophysiology of LQTS2

Figure 2E:
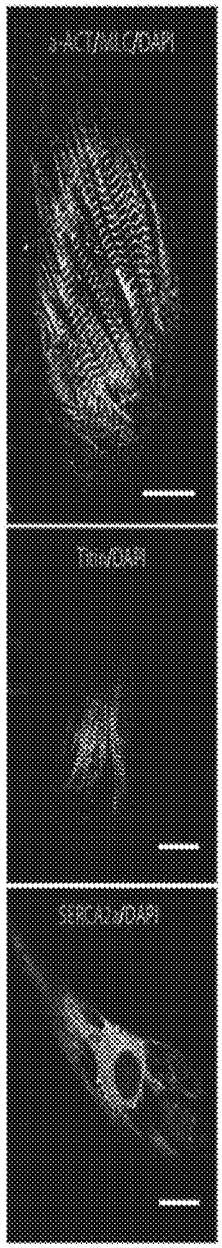
Figure 8:
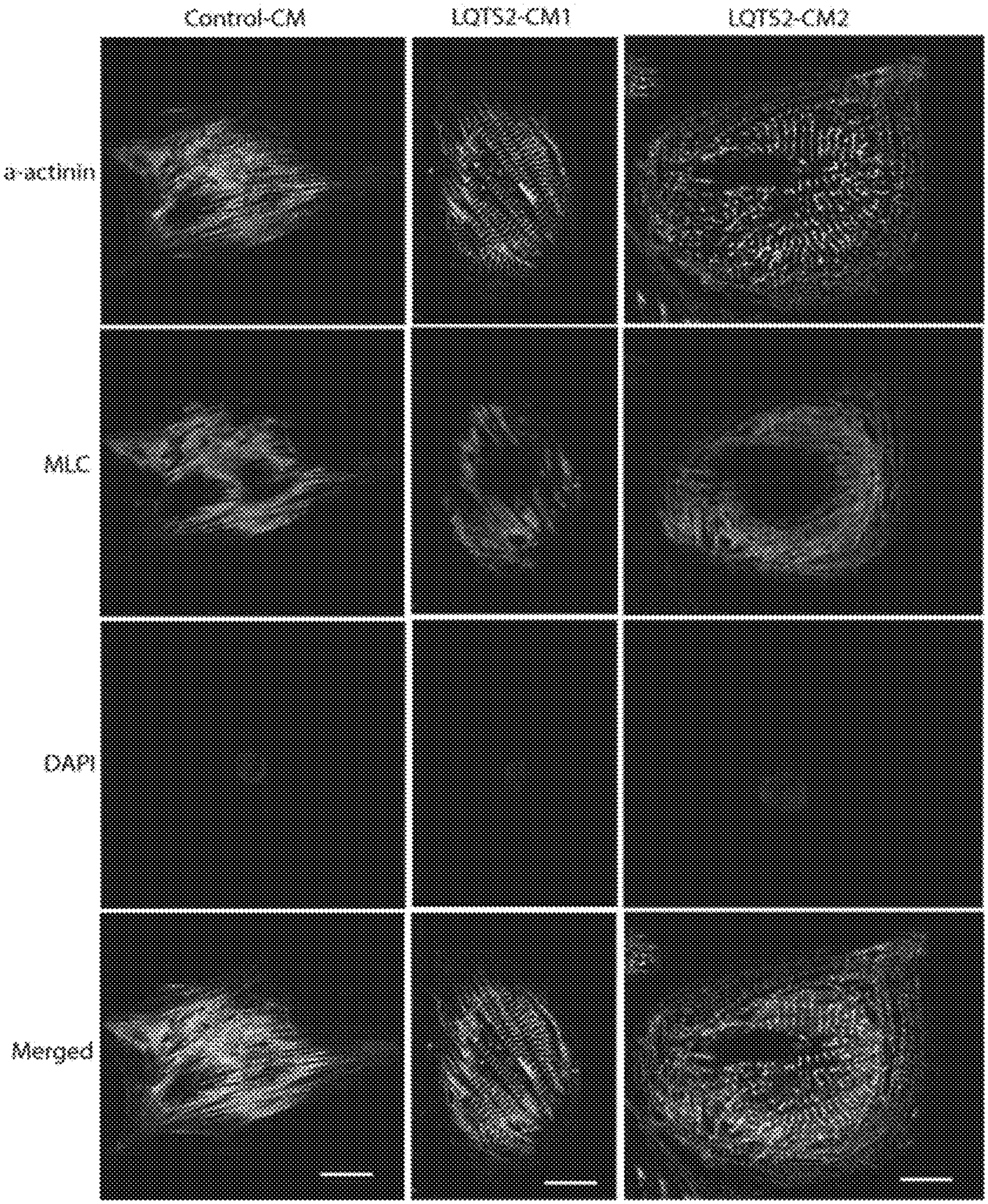
FIG. 8: Immunofluorescence of mature cardiac markers. Co-immunostaining of cardiac a-actinin (green) and myosin light chain (red) and counterstained with DAPI in control- and LQTS2-derived hiPSC cardiomyocytes on day 21 post differentiation. Bar 50 μm.
Figure 9:
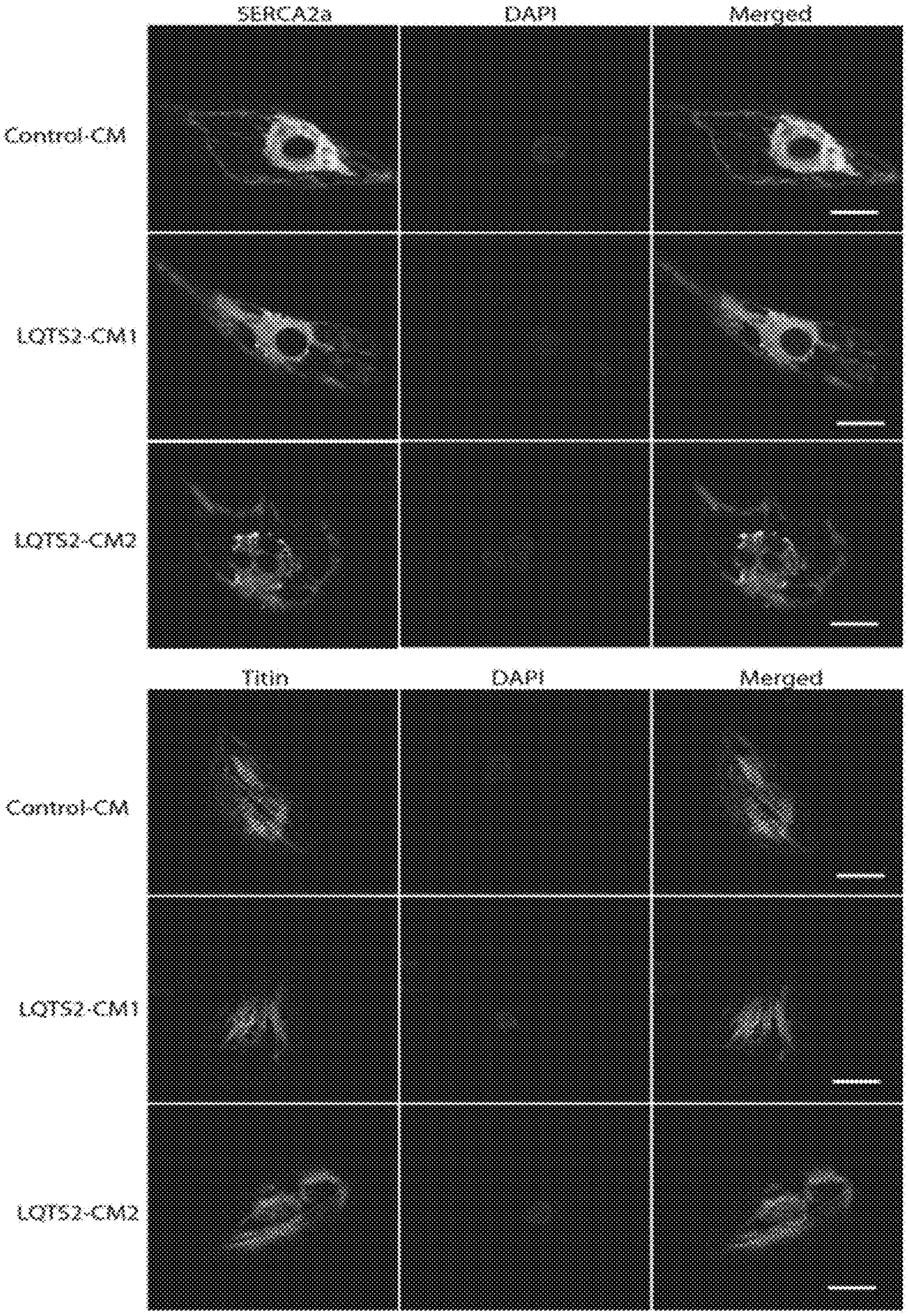
FIG. 9: Immunostaining of hiPSC-derived cardiomyocytes. Immunostaining of SERCA2a (top) and cardiac titin (below) and counterstained with DAPI in control- and LQTS2-derived hiPSC cardiomyocytes on day 21 post differentiation. Bar 50 μm.
Figure 10:
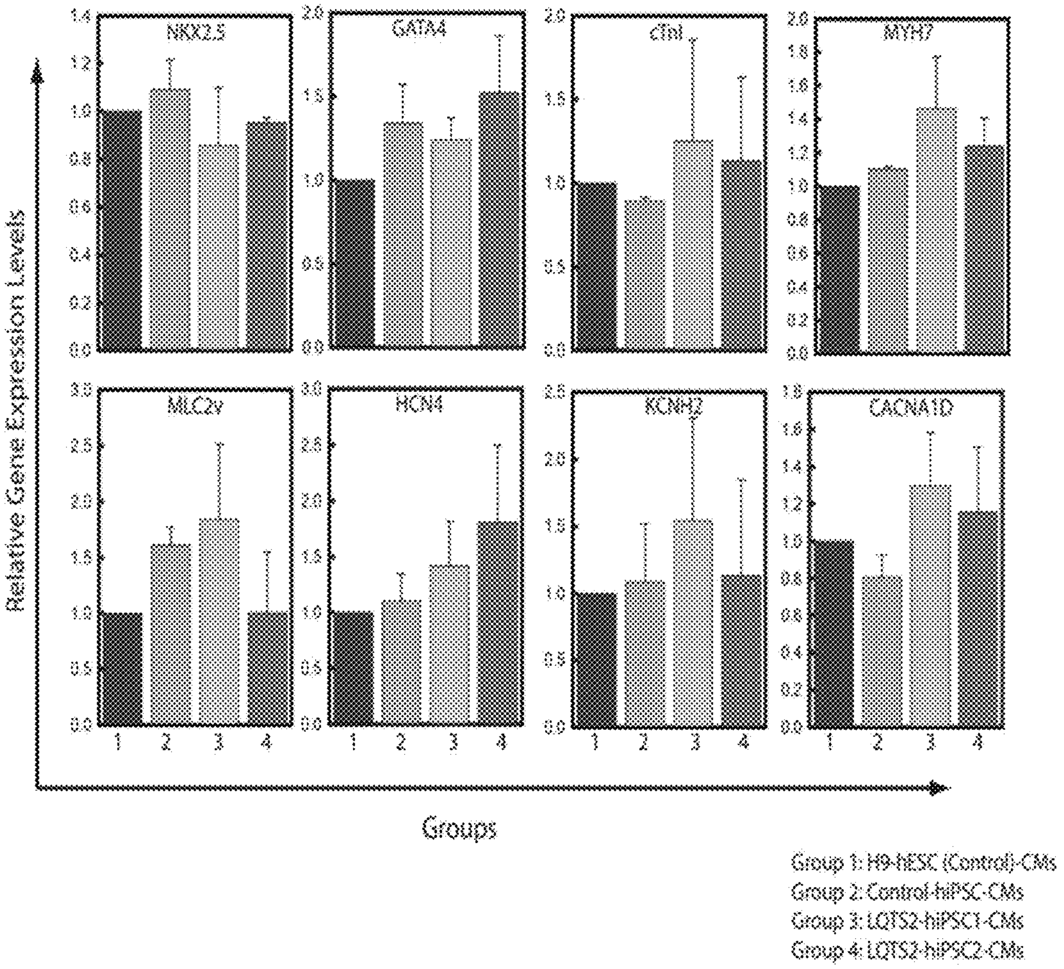
FIG. 10: Real-time gene expression analysis of hiPSC-derived cardiomyocytes. Relative gene expression of cardiac-specific transcriptional markers, NKX2.5 and GATA4, structural protein, cTnI, MYH7, MLC2v and ion channel, HCN2, KCNH2, CACNA1D in control- and LQTS2-hiPSC derived cardiomyocytes on day 21 post differentiation. Relative gene expression levels were calculated using a standard human embryonic stem cell line, H9. Bars represent mean and SEM. (n=9). No statistical difference was noted between groups.

Cardiac differentiation in control- and LQTS2-hiPSCs via EBs towards cardiomyocytes (CM) was performed. Spontaneously contracting areas were visible 12-14 days post-differentiation via EB based protocol in control- and LQTS2-hiPSCs with similar efficiencies. Positive staining of dissociated contracting clusters with sarcomeric α-actinin, myosin light chain-2, titin and SERCA2a, confirmed cardiac morphology (FIG. 2E; FIGS. 8-9). Furthermore, quantitative gene expression of cardiac-specific transcriptional, structural and functional markers confirmed normal cardiac ontogeny of both our control- and LQTS2-hiPSC lines (FIG. 10).

Figure 11:
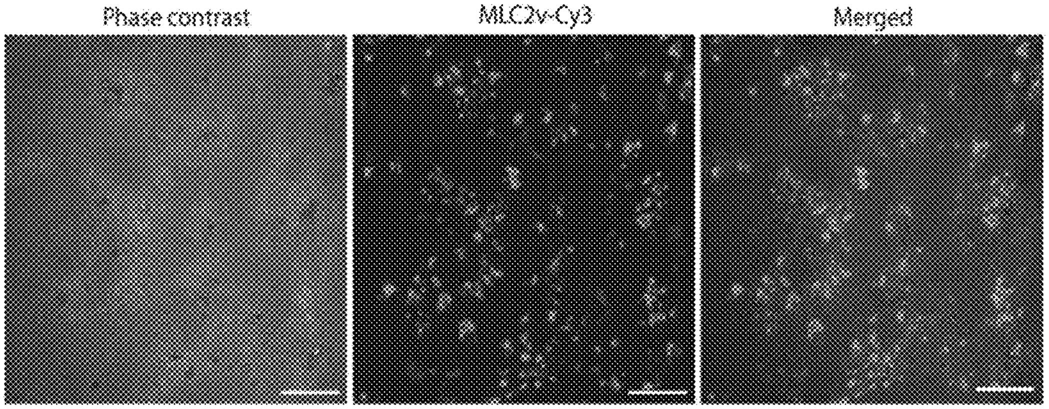
FIG. 11: Identification of LQTS2 ventricular myocytes. Live staining of LQTS2-myocytes to identify ventricular myocytes. Cells were stained with MLC2v specific Smartflare™ RNA probes conjugated with Cy3. Note majority of the cells express MLC2v mRNA, that was utilized to identify ventricular phenotype. Scale bar: 200 μm.
Figures 12A, 12B, 12C, 12D, 12E, 12F:
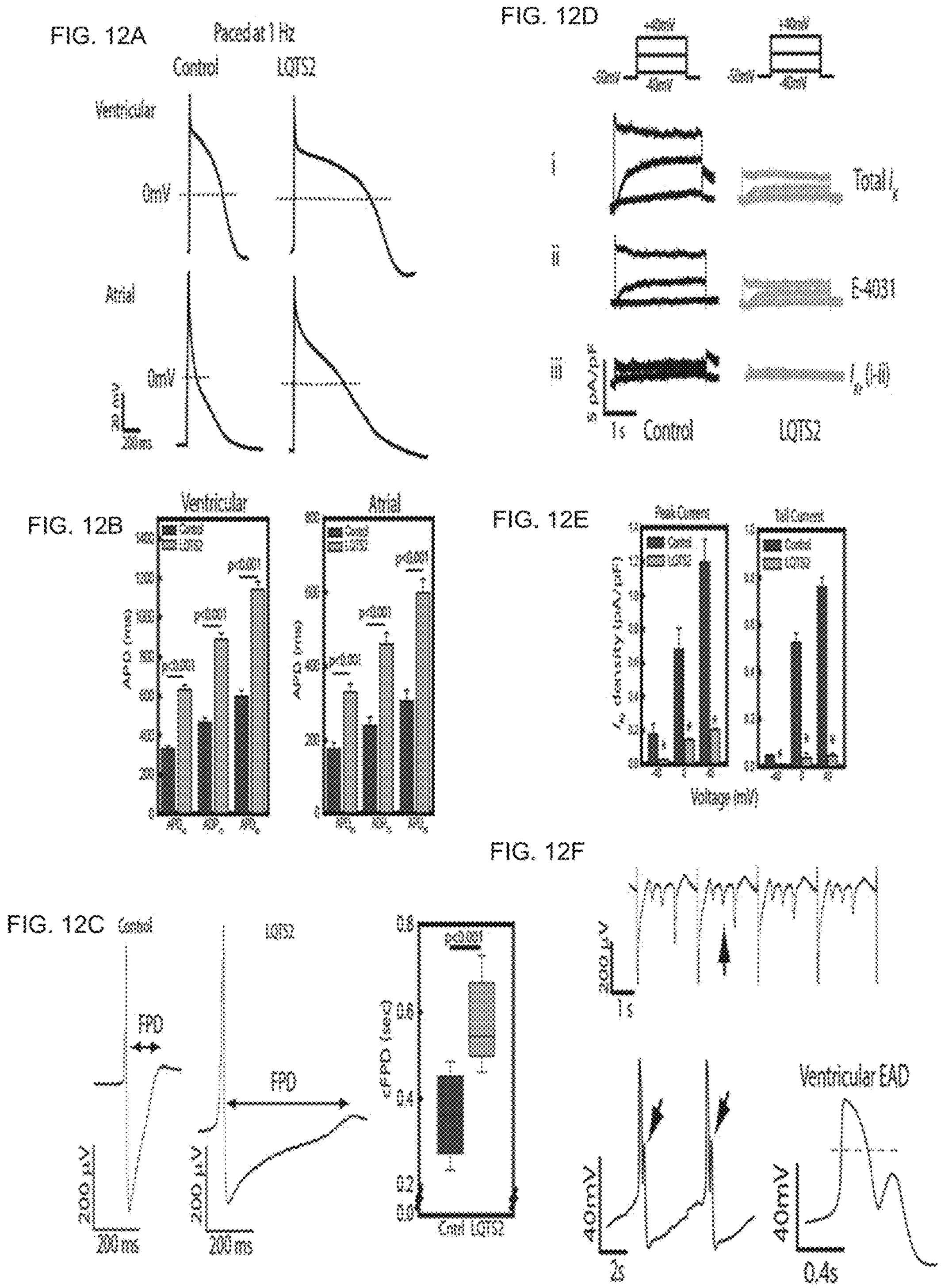
FIG. 12: Phenotypic characterization of LQTS2-hiPSC-derived cardiomyocytes. (A) AP traces from control- and LQTS2-CMs showing ventricular-like and atrial-like morphologies following 1 Hz pacing. (B) Summary shows ventricular- (n=7) and atrial-like (n=5) APD50-90 in LQTS2- and control-hiPSC-CMs. Bars represent mean±SEM. P values indicated by ANOVA. (C) Microelectrode array extracellular recordings from control- (left) and LQTS2 (right)-hiPSC-EBs. Box plot shows beating rate-matched FPDs (cFPDs) in LQTS2-EBs and controls, n=20. (D) Voltage-clamp recordings of the $I_{Kr}$ current, from control- (black) and LQTS- (grey) hiPSC-CMs (ventricular). i, baseline recordings. ii, recordings following administration of E-4031 (1 μM). iii, E-4031-sensitive current ($I_{Kr}$) defined by digital subtraction of the two currents (i-ii). (E) Summary of the $I_{Kr}$ peak and tail-current amplitudes measured following test depolarization pulses of −40, 0 and +40 mV, n=9. Error bars represent mean±SEM. *$P<0.05$ are compared to respective controls. (F) Top panel, Spontaneous arrhythmogenicity in LQTS2-EBs with multiple premature beats in MEA recordings. Bottom panel, Development of EADs in LQTS2 ventricular-like CMs during spontaneous recordings. Arrow head shows arrhythmogenicity.

We then performed cardiac electrophysiology in control- and LQTS2-CMs at single cell level using patch clamp technique and evaluating functional syncytium at multicellular levels by microelectrode array. MLC2v specific Smartflare™ RNA detection probes were utilized to identify ventricular myocytes (FIG. 11) and consistent with LQTS electrophysiology (Itzhaki I, et al., *Nature* 2011; 471:225-229; Sanguinetti M C, et al., *Nature* 2006; 440:463-469), current-clamp recording of LQTS2 ventricular and atrial myocytes showed prolonged action potential duration (APD) with $APD_{70/90}$ lengthening about 1.9-folds more than those in control myocytes with 1 Hz pacing (Table 2; FIG. 12A-B).

TABLE 2

Characterization of action potential of cardiomyocytes.

| | n | $APD_{50}$ (ms) | $APD_{70}$ (ms) | $APD_{90}$ (ms) | APA (mV) | Vmax (V/s) | RP (mV) |
|---|---|---|---|---|---|---|---|
| Control | | | | | | | |
| Ventricular | 7 | 332 ± 14.6 | 468 ± 21.8 | 600 ± 27.7 | 97.5 ± 2.2 | 24.9 ± 8.9 | −53.3 ± 2.3 |
| Atrial | 5 | 175 ± 17.7 | 240 ± 22.6 | 306 ± 29.2 | 83.7 ± 1.5 | 25.4 ± 7.6 | −51.7 + 2.6 |
| LQTS2 | | | | | | | |
| Ventricular | 7 | 633 ± 24.2* | 890 ± 30.2* | 1144 ± 38.8* | 101.9 ± 1.6 | 23.6 ± 5.0 | −52.8 ± 2.5 |
| Atrial | 5 | 331 ± 22.1* | 460 ± 31.2* | 599 ± 38.6* | 84.3 ± 1.0 | 27.6 ± 6.8 | −53.5 ± 2.3 |

TABLE 2-continued

| Characterization of action potential of cardiomyocytes. | | | | | | | |
|---|---|---|---|---|---|---|---|
| | n | $APD_{50}$ (ms) | $APD_{70}$ (ms) | $APD_{90}$ (ms) | APA (mV) | Vmax (V/s) | RP (mV) |
| LQTS2 + ALLN | | | | | | | |
| Ventricular | 7 | 388 ± 16.2# | 534 ± 20.5# | 702 ± 29.6# | 103.3 ± 1.6 | 25.3 ± 4.0 | −52.7 ± 2.3 |
| Atrial | 5 | 228 ± 19.2# | 320 ± 27.9# | 406 ± 34.4# | 84.9 ± 2.0 | 23.8 ± 4.0 | −51.2 ± 2.6 |

Action-potential recordings from the healthy control- and LQTS2 hiPSCs-derived cardiomyocytes following 1 Hz pacing. Results show APA (action potential amplitude); RP (resting membrane potential); APD-50/70/90 (action potential duration 50/70/90) and Vmax (upstroke velocity max). *$p<0.001$ compared to controls; #$p<0.001$ compared to LQTS2.

Consistent with single cell patch-clamp studies, extracellular field potential recordings of the LQTS2-EBs (FIG. 12C) demonstrated significant prolongation in beating rate-corrected field potential duration (cFPD) when compared to control-EBs (Control-EBs vs LQTS2-EBs: 0.368±0.02 s vs. 0.579±0.02 s, n=20, $p<0.001$).

Furthermore, in single cell voltage-clamp studies, LQTS2 ventricular myocytes (detected using MLC2v Smartflare™ RNA detection probes, n=9) showed a substantially reduced E-4031 (a specific $I_{Kr}$ blocker)-sensitive currents (FIG. 12D). At +40 mV, peak and tail $I_{Kr}$ currents depressed by approximately 80% and 90% respectively than in control cells (FIG. 12E).

Consistent with single cell patch-clamp studies, extracellular field potential recordings of the LQTS2-EBs (n=20; FIG. 12F) demonstrated significant prolongation in beating rate-corrected field potential duration (cFPD) when compared to control-EBs (n=20). Interestingly, LQTS2-EBs (n=75/100 EBs screened) demonstrated spontaneous arrhythmogenic events (75%; FIG. 12F) that were not observed in control-EBs (n=50). Similarly, some arrhythmogenic events were also recorded at single cell levels during spontaneous contraction (FIG. 12F).

Figure 13A:
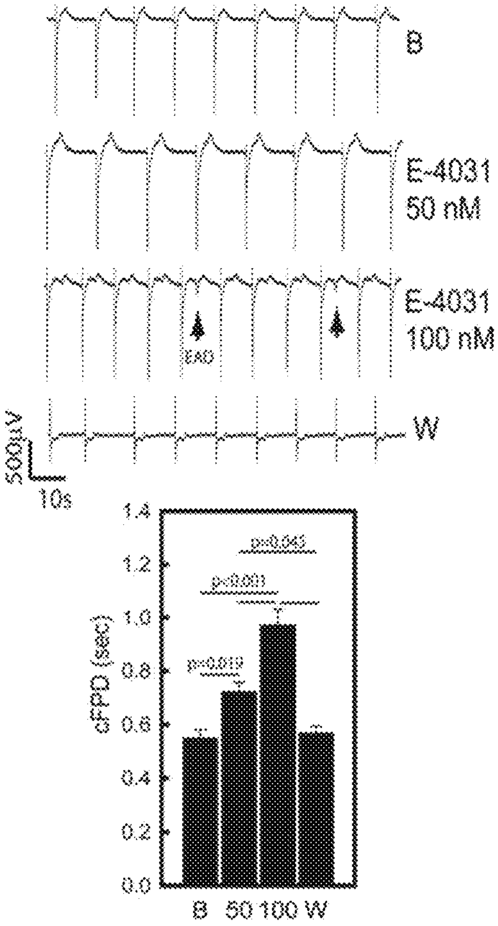
FIG. 13: Drug induced responses in LQTS2-CM. (A) Multi-electrode array (MEA) recordings demonstrating the effects of E-4031 (IKr blocker) on LQTS2-EBs. E-4031 generates early after-depolarizations (EADs) in these cells along with prolongation of repolarization durations as demonstrated by beating rate-corrected field potential durations (cFPDs). Bars represent mean±SEM, n=15. P values calculated by ANOVA. B—Baseline, W—Washout, 50/100-50/100 nM doses of E-4031. (B) Positive chronotropic responses of LQTS2EBs (n=15) to isoproterenol (Iso/I; 1 uM) and its reversal with atenolol (At/A; 10 μM). Bars represent mean±SEM and P values as indicated by ANOVA.
Figure 13B:
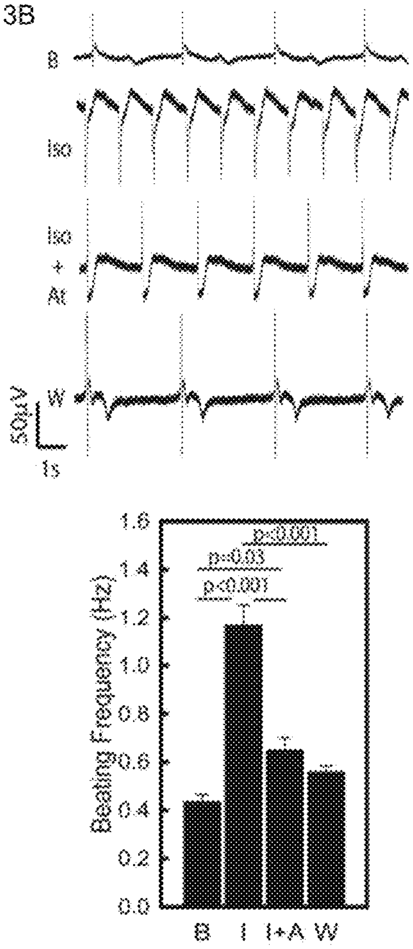

Contracting EBs from control and LQTS2 were also evaluated with drugs that may ameliorate or aggravate the disease phenotype (Patel C, et al., *Pharmacology & therapeutics* 2008; 118:138-151). 100 nM E-4031, a methanesulfonanilide class III antiarrhythmic agent known to inhibit KV11.1 (hERG) channels, increased cFPDs significantly in both cell types, but LQTS2-contracting EBs demonstrated pronounced occurrence of early after-depolarizations (EADs; n=14/15; FIG. 13) as compared to the controls (n=2/15). We next performed a stress test on contracting clusters via sympathetic stimulation by the β-adrenoreceptor agonist, isoproterenol, as LQTS2 patients are known to have an increased sympathetic tone to adrenergic stimulated arrhythmias. Furthermore, addition of isoproterenol to LQTS2-EBs increased beating frequencies and reduced cFPDs, with aggravating arrhythmogenic episodes. These increased contracting rates were accompanied with reduced cFPDs (LQTS2-baseline vs. Iso: 0.657±0.07 s vs. 0.212±0.02 s, n=15). Subsequent treatment with β-adrenoreceptor antagonist, atenolol reduced the beating frequencies as well as restored cFPDs (FIG. 13). These results collectively confirmed that the LQTS2-CMs manifested hERG dysfunction that is of value for disease modeling.

LQTS2 Myocytes Express More Mutant Allele and Non-Glycosylated hERG

Figure 15A:
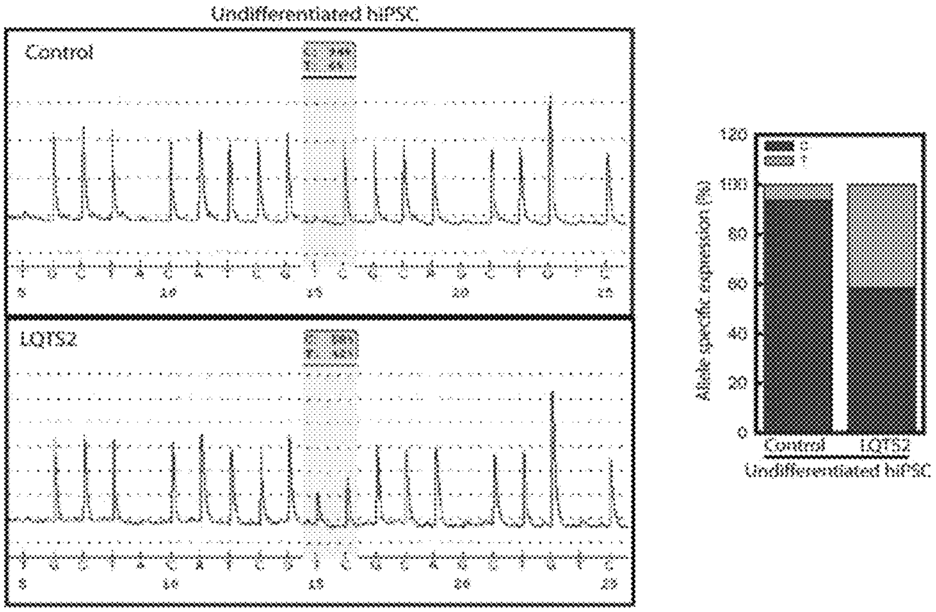
FIG. 15: Allele Specific KCNH2 expression by Pyrosequencing. (a) Pyrosequencing analysis of control-undifferentiated hiPSC and LQTS2-undifferentiated hiPSC. Note no mutant allele (T) dominance is observed over wild-type allele (C) in LQTS2-hiPSC when control-undifferentiated hiPSC was compared with LQTS2-undifferentiated hiPSC. (b) Pyrosequencing analysis of control- and LQTS2-CMs. Note significant mutant allele (T) dominance is observed over wild-type allele (C) in LQTS2-CMs.
Figure 15B:
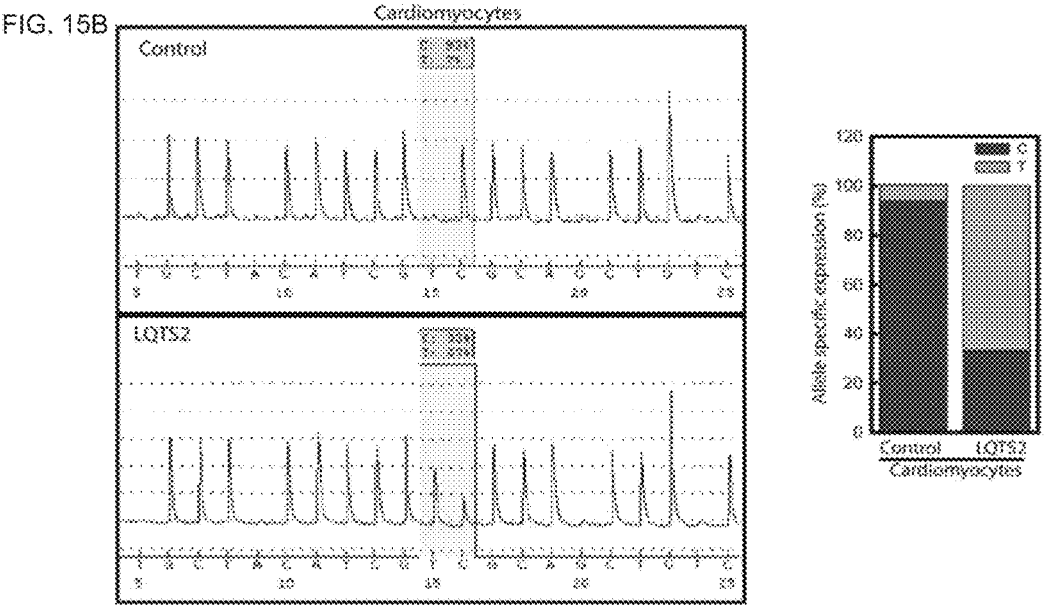

In order to correlate electrophysiological changes in LQTS2-CMs with dysfunctional hERG, we performed PCR and observed that the mutant KCNH2 allele was significantly overexpressed in comparison to wild-type allele in LQTS2-CMs (FIG. 14A). Further, allele-specific pyrosequencing confirmed that in LQTS2-CMs, 67% of the KCNH2 transcripts were dominated by the mutant allele (FIG. 14B), whereas both alleles showed equal dominance in undifferentiated LQTS2-iPSC (FIG. 15).

Figure 16:
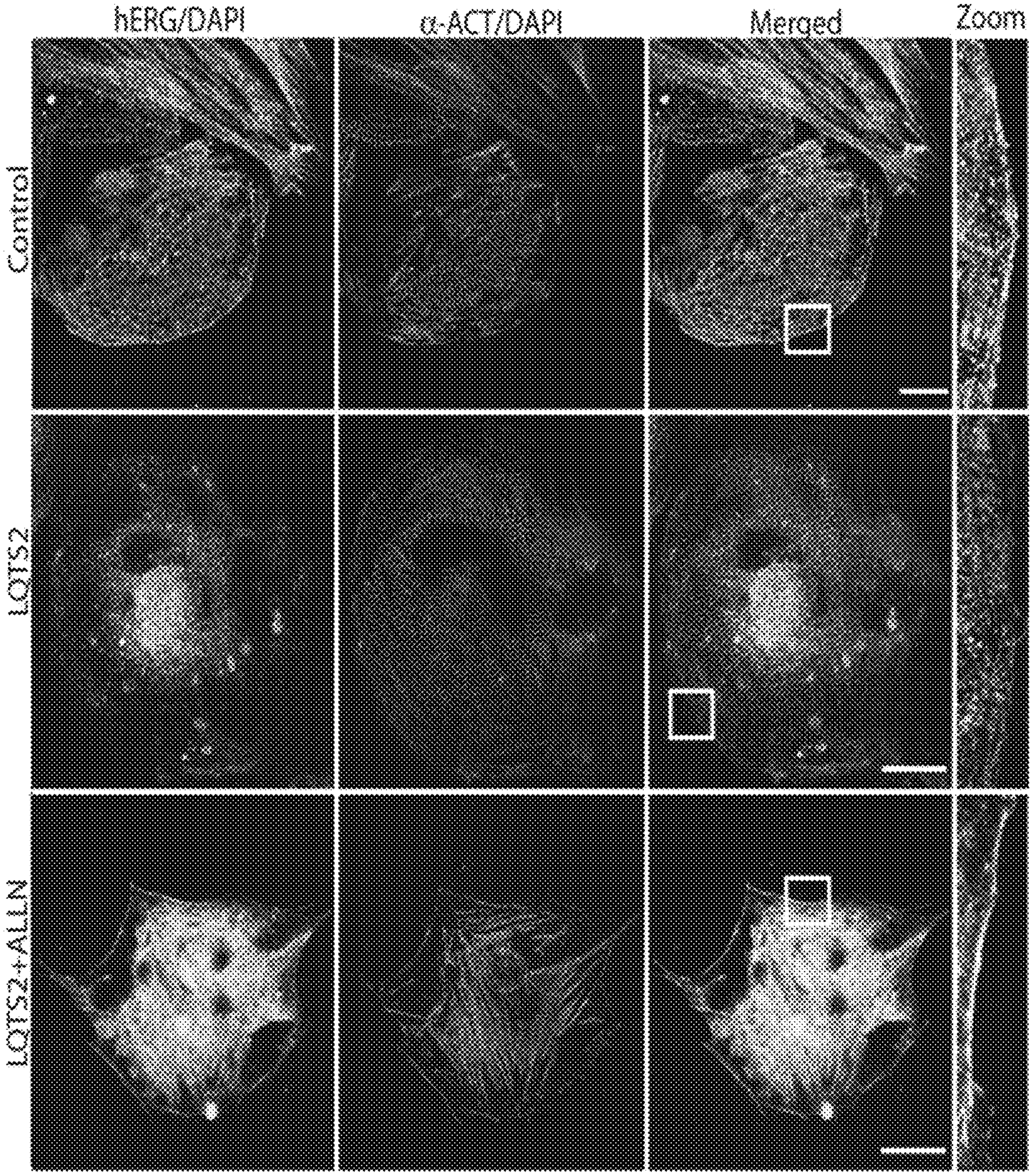
FIG. 16: hERG staining showing localization of hERG (green/left column) on the sarcolemmal membrane of alpha-actinin (red/middle column) stained cardiomyocytes. Top panel: Control-CM; mid panel: LQTS2-CM; bottom panel: ALLN-treated LQTS2-CM. Zoomed image from boxed region of each merged image showing enhanced localization of hERG (yellow/right margin) onto sarcolemma of ALLN-treated LQTS2-CM. Scale bar: 20 um.
Figure 17A:
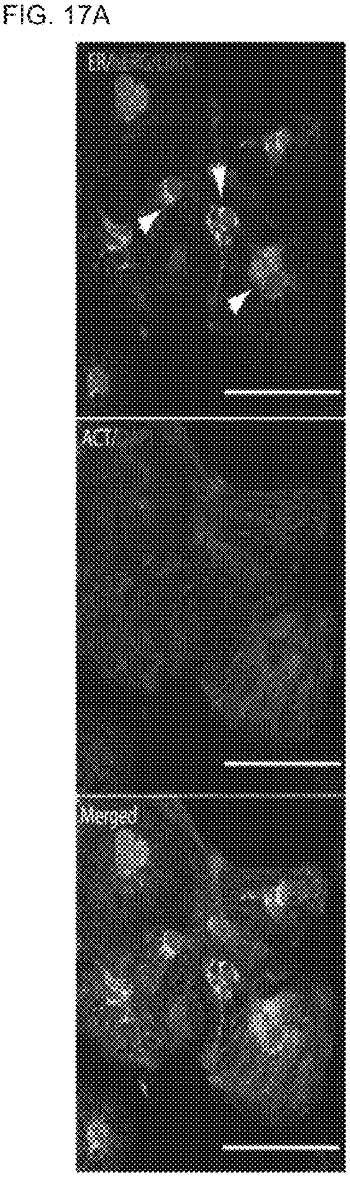
FIG. 17: hERG sequester in endoplasmic reticulum and interact with hsp70 in LQTS2-CMs. (a) Immunofluorescence images showing co-localization of hERG (red) with calnexin (green), a known ER marker, counterstained with a-actinin (white) and DAPI in LQTS2-CMs. Note the arrowheads show co-localization of hERG with calnexin. Scale bar: 100 μm. (b) Immunofluorescence images showing co-localization of hERG (red) with hsp70 (green), counterstained with a-actinin (white) and DAPI in LQTS2-CMs. Note the arrowheads show co-localization of hERG with hsp70. Scale bar: 100 μm. (c) Immunprecipitation (IP) of hERG with hsp70 antibody along with negative control (Neg, No hERG Ab). Western blot (lysate) showing hsp70 in total cell lysate.
Figure 17B:
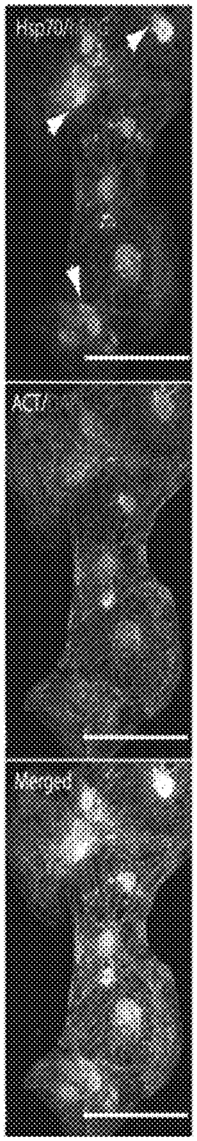
Figure 17C:
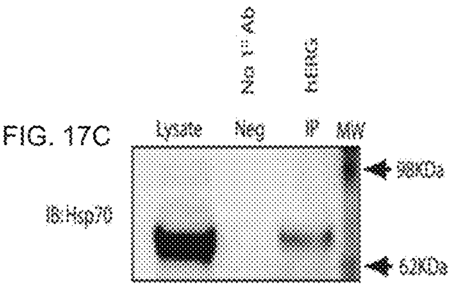

This allelic dominance was consistent with LQTS2-CMs hERG western blots that showed more non-glycosylated (immature) hERG as compared to controls (FIG. 14C). Immunostaining of hERG in LQTS2-CMs further confirmed a significant reduction (3-fold) in sarcolemmal localization densities (FIGS. 14Dvi and E-F) compared to control-CMs (FIGS. 14Diii and E-F, FIG. 16). Furthermore, LQTS2-CMs showed a significant sequestering of hERG (4-fold; FIG. 14Dv, F) in the peri-nuclear area (endoplasmic reticulum; FIG. 17) as compared to control-CMs (FIG. 14Dii, F). These results taken together suggest that the mutant allele caused sequestration of hERG channel in the endoplasmic reticulum, indicative of a trafficking defect of hERG in the LQTS2-CMs.

Chaperone and Trafficking Defects in LQTS2-CMs

Figure 18A:
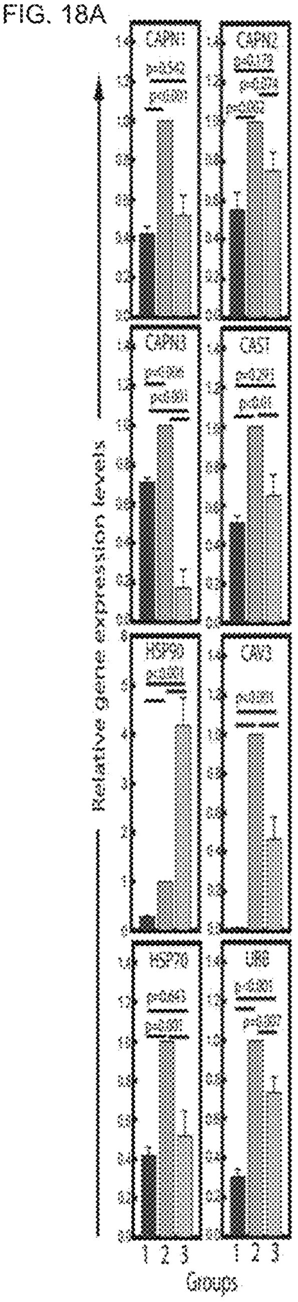
FIG. 18: LQTS2-CMs show trafficking defects. (A) Quantitative gene expression for determinants of trafficking pre- and post-ALLN treatment in LQTS2-CMs compared to control-CMs (n=6). Bars represent mean±SEM. P values indicated by ANOVA. Groups: 1—Control; 2—LQTS2; 3—LQTS2+ALLN. (B) Immunostaining of α-actinin (i,iii, v) and calpastatin (ii,iv,vi) in control (i-ii), LQTS2 (iii-iv) and LQTS2+ALLN (v-vi) and counterstained with DAPI. Scale bar, 50 μm. (C) Quantitative gene expression for trafficking determinants in control- and LQTS2-hiPSC and fibroblast (n=6). No significant change was observed between the two groups. Bars represent mean±SEM. (D) Western blots for determinants of trafficking pre- and post-ALLN treatment in LQTS2-CMs along with densitometric evaluation of the bands. P values were calculated by student t-test. The band intensities were normalized to β-actin (loading control).
Figure 18B:
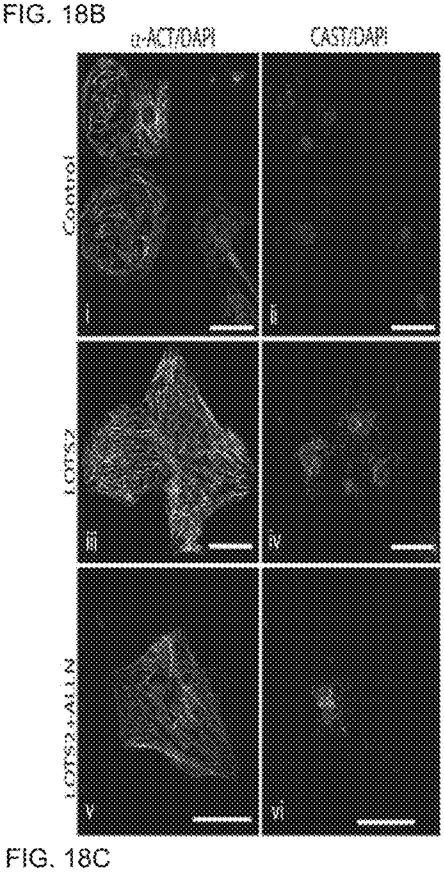
Figure 18C:
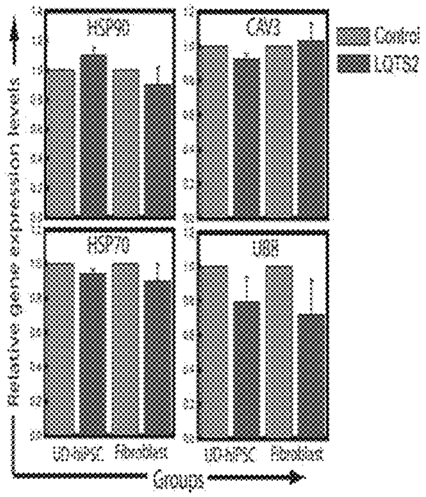

To confirm hERG trafficking dysfunction, we investigated key players in calpain and proteosomal systems that are integral in protein trafficking. Quantitative gene expression analysis of LQTS2-CMs showed a significant upregulation of $Ca^{2+}$-activated cysteine protease family (Calpain) members, CAPN1 (2.5-folds), CAPN2 (2-folds) and CAPN3 (1.5-folds) compared to controls (FIG. 18A, group 2 versus group 1). Expression of CAST (Calpastatin) also showed a 2-fold increase in LQTS2-CMs (FIG. 18A), but was substantially accumulated in the peri-nuclear area (FIG. 18Biv) as compared to control-CMs (FIG. 18Bi). We also observed significantly increased gene expression of HSP90 (5-fold), HSP70 (2.5-fold), UBB (Ubiquitin; 3-fold) and CAV3 (Caveolin 3; 50-fold; FIG. 18A). However, unlike LQTS2-CMs, such changes were not observed in undifferentiated LQTS2-hiPSCs or patient fibroblasts (FIG. 18C). Immunostaining of hERG and hsp70 in LQTS2-CMs showed that they co-localized in the endoplasmic reticulum (FIG. 17), while immunoprecipitation studies confirmed interactions of hERG and hsp70 (FIG. 17).

Re-Trafficking of hERG by ALLN

Figure 18D:
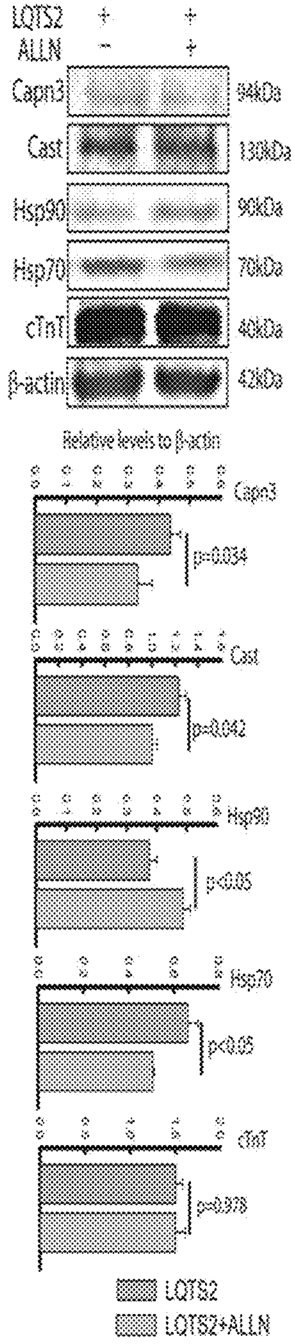

As trafficking was implicated in our results, the LQTS2-CMs were treated with 10 μM ALLN (N—[N—(N-Acetyl-L-leucyl)-L-leucyl]-L-norleucine; $C_{20}H_{37}N_3O_4$), a known Calpain 1/2 and proteasome inhibitor. Post-ALLN treatment (42 h), western blots showed a significant increase in glycosylated (mature) hERG in LQTS2-CMs as compared to untreated LQTS2-CMs (FIG. 14C). In comparison to untreated LQTS2-CMs, membrane density plot of hERG immunostaining demonstrated increased peak numbers (FIG. 14E) and enhanced sarcolemmal localization (2-fold) with corresponding reduction (66%) in pen-nuclear hERG retention following ALLN treatment (FIGS. 14Dvi and F). These results suggested that blocking the proteasomal pathway with ALLN could re-traffick sequestered hERG towards sarcolemma of LQTS2-CMs. ALLN-treated LQTS2-CMs also showed down-regulated expression of CAPN1 (50%), CAPN2 (25%) and CAPN3 (80%) with corresponding reduction in CAST (40%), UBB (25%), HSP70 (50%) and CAV3 (60%) gene expression levels with the exception of HSP90 (4-fold increase) (FIG. 18A, group 3). These changes were corroborated by western blot of calpain 3, Calpastatin, Hsp90 and Hsp70 proteins that confirmed trafficking pathway modulation by ALLN (FIG. 18D). Furthermore, reduced calpastatin production was reflected by subdued pen-nuclear staining in the ALLN treated LQTS2-CMs (FIG. 18Bvi).

ALLN Rescued LQTS2-CM Show Phenotypic Correction of Repolarization

Figures 19A, 19B, 19C, 19D, 19E, 19F, 19G, 19H, 19I:
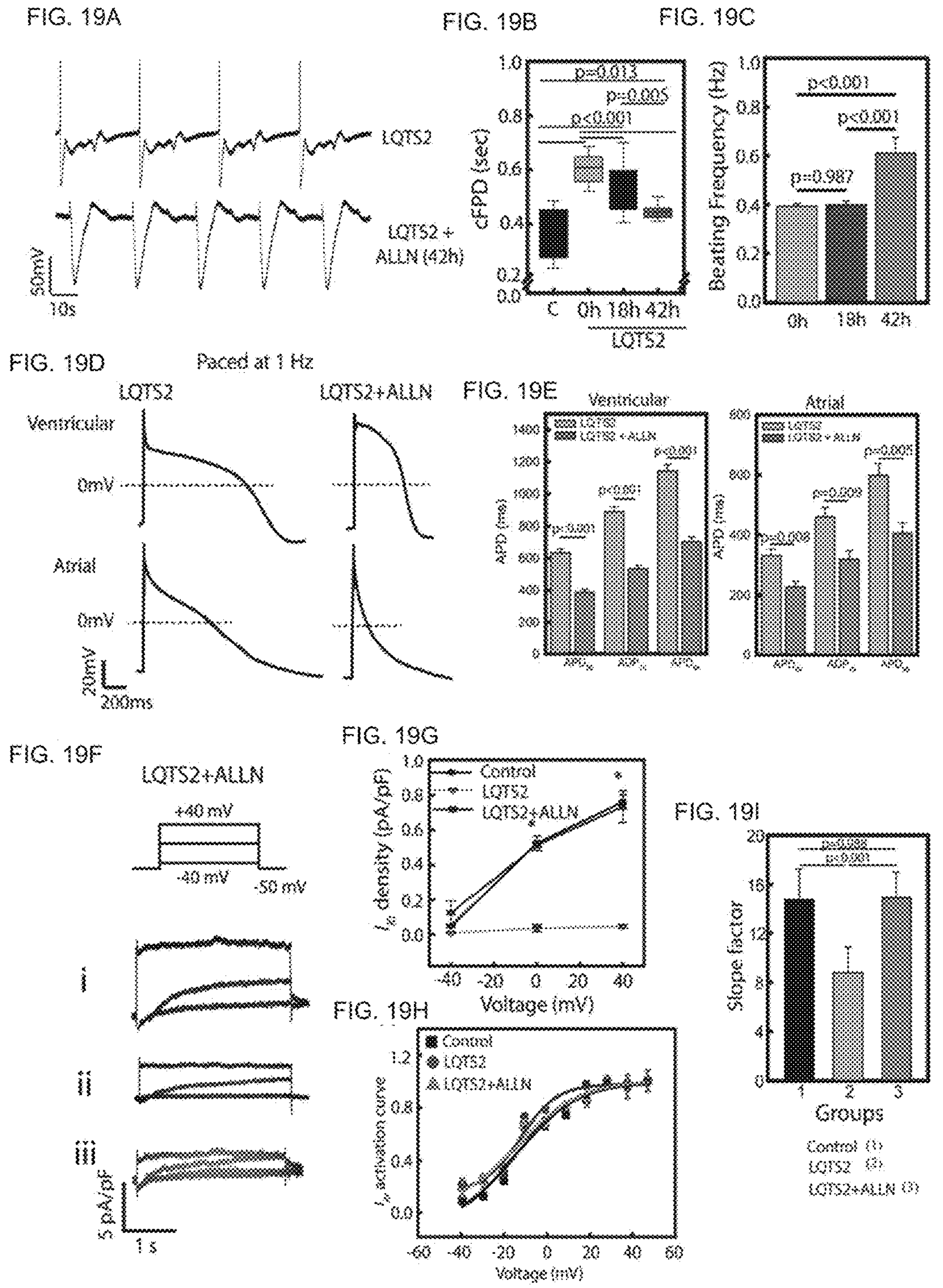
FIG. 19: ALLN-induced corrective trafficking in LQTS2-CMs. (A) Extracellular recordings from LQTS2 pre-(top) and post-ALLN (10 μM, below) treatment at 42 h. (B-C) Summary of time-dependent cFPDs and beating frequencies in pre- (n=82) and post-ALLN treated LQTS2-CMs at 18 h (n=25) and 42 h (n=34). P values indicated by ANOVA. (D) AP recordings from LQTS2-CMs pre- and post-ALLN treatment showing ventricular-like and atrial-like morphologies following 1 Hz pacing. (E) Summary shows ventricular- (n=7) and atrial-like (n=5) APD50-90 in LQTS2-CMs and ALLN treated LQTS2-CMs. Bars represent mean±SEM. P values indicated by ANOVA. (F) Voltage-clamp recordings of the $I_{Kr}$ current from LQTS2+ALLN treated ventricular CMs. i, baseline recordings. ii, recordings following E-4031 (1 μM) treatment. iii, E-4031-sensitive current ($I_{Kr}$) defined by digital subtraction of the two currents (i-ii). (G) Summary of the $I_{Kr}$ tail-current densities measured following test depolarization pulses of −40, 0 and +40 mV, n=6. Error bars show SEM. *p<0.05. (H) Non-linear regression analysis of normalized tail currents (Norm TC) against pre-pulse potential showing no significant change in activation voltage for $I_{Kr}$ in the three groups. (I) Summary of slope factor calculated from non-linear regression analysis. Bars represent mean and SEM, n=6. Groups: 1—Control, 2—LQTS2, 3—LQTS2+ALLN.
Figure 20:
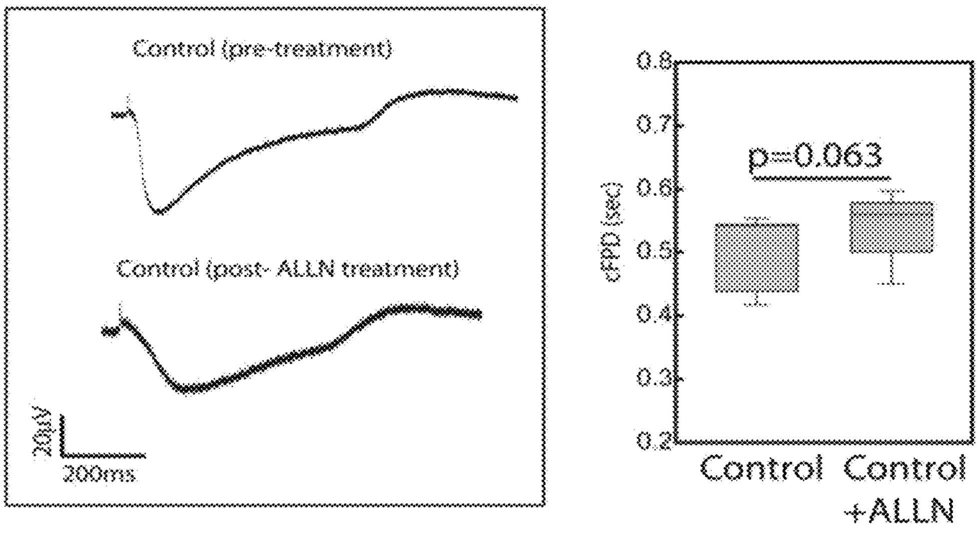
FIG. 20: ALLN treatment on control-CMs. MEA recording demonstrating no significant change in waveforms post-ALLN treatment in control-CMs at 48 h. Box plot shows beating rate-matched FPDs (cFPDs) in control-CMs, n=9.

Next, we evaluated if hERG re-trafficking induced by ALLN could reduce prolonged repolarization of LQTS2-CMs. MEA recordings of ALLN-treated LQTS2-EBs clearly demonstrated a time-dependent reduction in cFPDs as compared to untreated LQTS2-EBs (FIG. 19A-B). ALLN reduced spontaneous arrhythmogenic episodes in the contracting EBs (FIG. 19A) and increased beating frequencies at 42 h exposure (FIG. 19C) with more rhythmic contractions. In contrast, neither significant change in cFPDs nor waveform changes were observed in control-CMs treated with ALLN (FIG. 20).

Figure 21A:
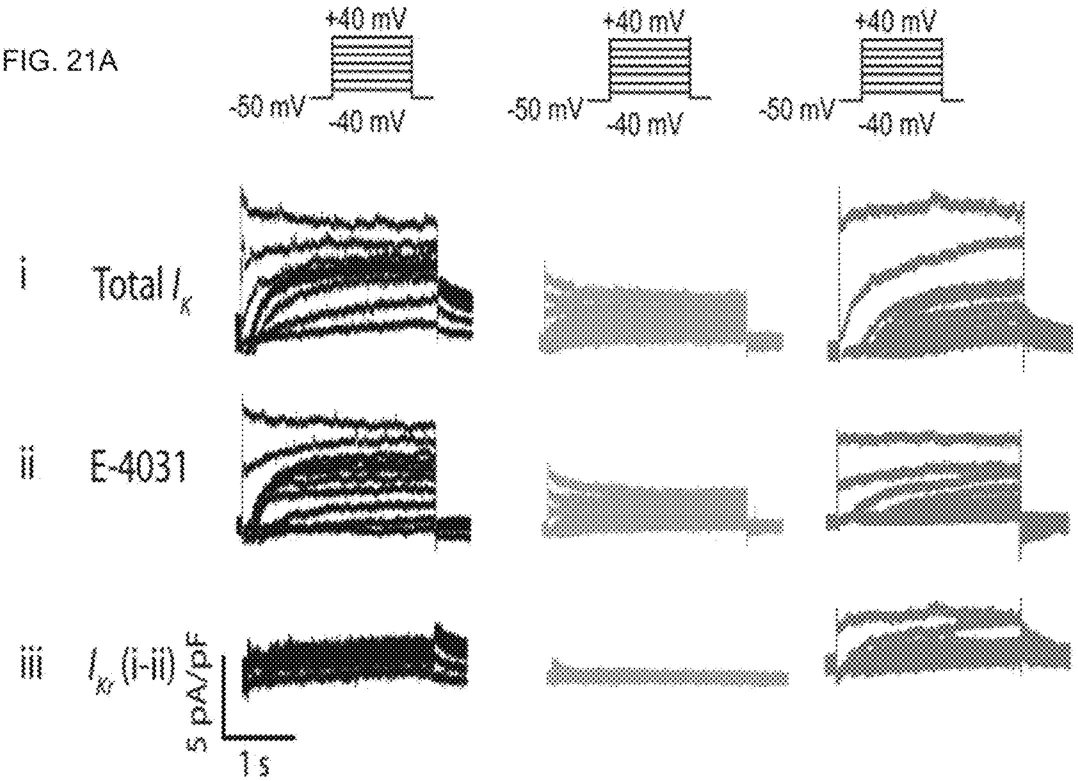
FIG. 21: ALLN-induced changes in IKr currents in LQTS2-CMs. (a) Voltage-clamp recordings of IK current in control (left), LQTS2 (centre) and LQTS2+ALLN (right). (i) baseline recording, (ii) recording after 1 μM E-4031, (iii) E-4031-sensitive current (IKr) defined by digital subtraction of the two currents (i-ii). (b) Summary of the IKr peak and tail current amplitudes measured following test depolarization pulses of −40 to +40 mV pre and post ALLN treatment in LQTS2-CMs.
Figure 21B:
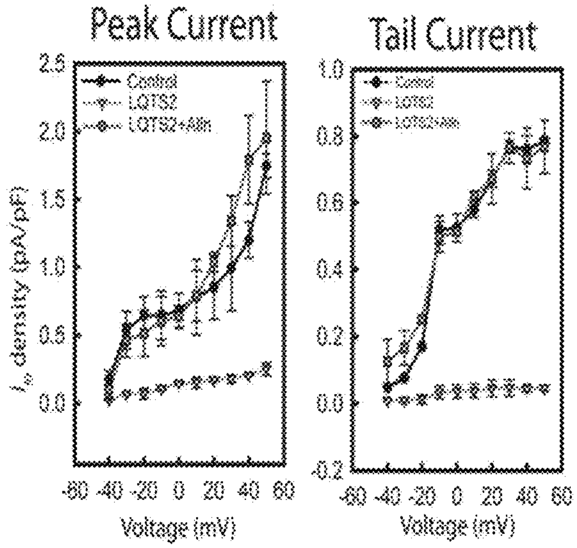
Figure 22A:
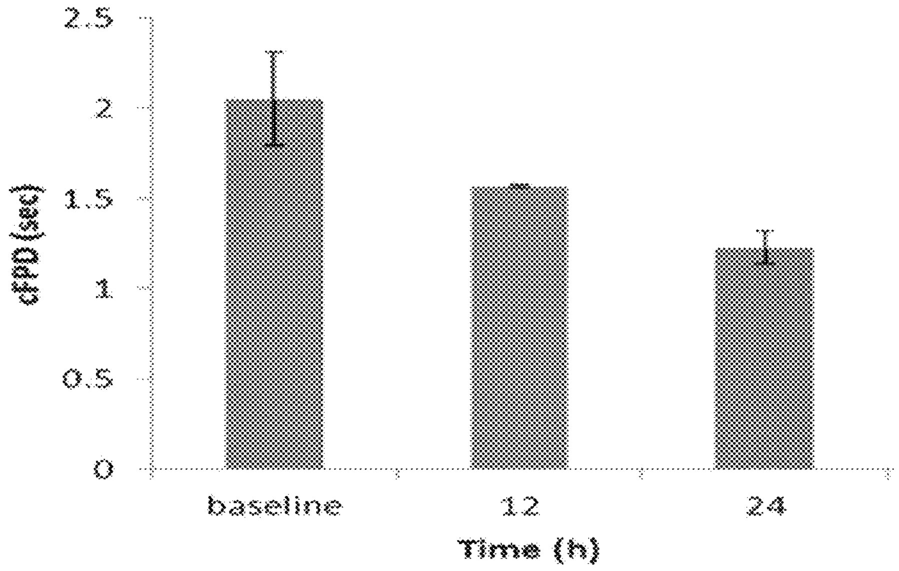
FIG. 22: Additional evidence showing reversal of LQTS2 requires re-trafficking and proper protein folding. (a) re-trafficking of mutant KCNH2 by using a pharmaceutical investigative drug VX-809 (10 μM) and (b) a pharmaceutically approved butyrate analog, sodium 4-phenylbutyrate (4BPA, 400 μM), reverses prolonged repolarization in human LQTS2 CMs as demonstrated by shortening of repolarization duration.
Figure 22B:
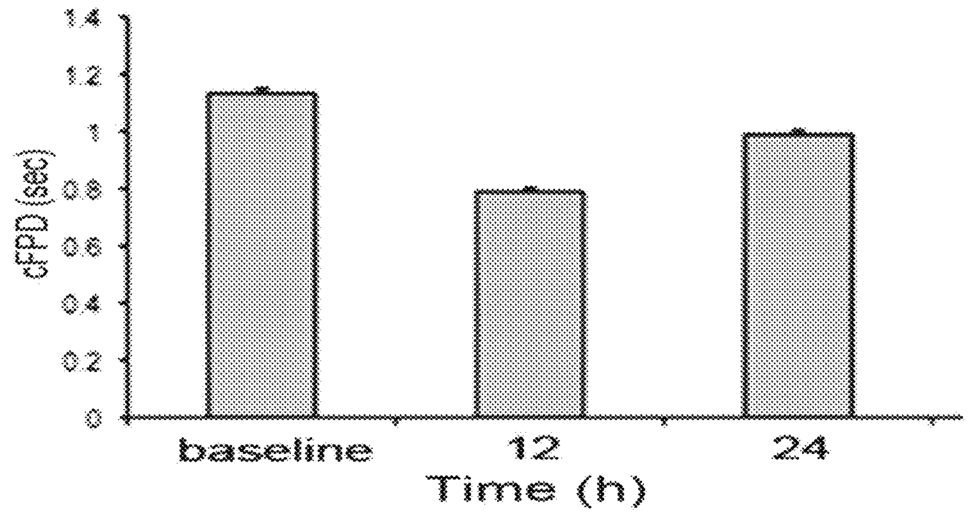

Single cell current-clamp recordings showed a marked reduction (1.5-fold) in $APD_{70/90}$ in both ventricular as well as atrial myocytes (FIG. 19D-E) at 42 h following ALLN treatment. Furthermore, voltage-clamp studies with E-4031 showed a recovery of $I_{Kr}$ currents in LQTS2-CMs (FIG. 19F-G; n=6) to similar levels as in control-CMs (FIG. 21). While, there was no significant shift in $V_{1/2}$ activation of $I_{Kr}$ between control-CMs (−10.0±4.6 mV; n=9), LQTS2-CMs (−14.2±6.0 mV; n=9) and ALLN treated LQTS2-CMs (−13.8±3.9 mV; n=6) (FIG. 19H), a significant restoration of slope factor post ALLN treatment was observed (FIG. 19I). Importantly, alternative pharmaceutical agent, VX-809 that targets protein trafficking pathway, and sodium 4-phenylbutyrate (4PBA) also demonstrated similar rescue of the LQTS2-CM by shortening the cFPD (FIG. 22). These studies demonstrate that re-trafficking strategies could potentially rescue LQTS2 phenotype in hiPSC-derived cardiomyocytes.

Discussion

In this study, we isolated skin fibroblasts from a patient carrying an autosomal dominant missense KCNH2 mutation with C1682T (A561V) substitution in the S5 transmembrane domain (Ficker E, et al., *Journal of molecular and cellular cardiology* 2000; 32:2327-2337) that is implicated in trafficking defective LQTS2.

Similar to other KCNH2 mutations, A561V has been associated with variable clinical penetrance ranging from 25 to 90% (Priori S G, et al., *Circulation* 1999; 99:529-533; Napolitano C, et al., *Circulation* 1997; 96(suppl I):I-212; Priori S G, et al., *Circulation* 1999; 99:518-528). More interestingly, contrary to other known KCNH2 mutations (Anderson C L, et al., *Circulation* 2006; 113:365-373), A561V mutant has been reported to be not responsive to pharmacological rescue (Ficker E, et al., *Journal of molecular and cellular cardiology* 2000; 32:2327-2337; Ficker E, et al., *Circulation research* 2003; 92:e87-100) and insensitive to temperature-mediated functional recovery (Anderson C L, et al., *Circulation* 2006; 113:365-373). The amino acid at position 561 is a hot-spot for LQTS2 mutations (Schwartz P J, et al., *Circulation,* 1997: I-212; Dausse E, et al., *Journal of molecular and cellular cardiology* 1996; 28:1609-1615) where 2 other known mutations at A561P and A561T were similarly reported to lead to drastic reduction in $I_{Kr}$ currents (Ficker E, et al., *Journal of molecular and cellular cardiology* 2000; 32:2327-2337). Previous studies (Matsa E, et al., *Eur Heart J* 2011; 32:952-962) have demonstrated that KCNH2 mutants hiPSC-CMs treated with channel modulators could shorten action potential durations. Alternative approaches that target mutants with defective channel assembly that are insensitive to known pharmacological rescue (Ficker E, et al., *Journal of molecular and cellular cardiology* 2000; 32:2327-2337), such as A561V mutant in this study, would help to better understand diversity of LQTS2 manifestations.

LQT2 hiPSC cardiomyocytes exhibited prolonged APD/cFPD and showed increased sensitivity to isoproterenol with frequent occurrence of EADs. Moreover, more than 75% of the beating clusters demonstrated spontaneous arrhythmogenic contractions. This high spontaneous arrhythmogenicity could be attributed to 90% reduction in $I_{Kr}$ currents as shown by our voltage-clamp studies. Similarly, hiPSC derived cardiomyocytes with A614V (in the pore region, transmembrane domain) (Itzhaki I, et al., *Nature* 2011; 471:225-229) and R176W mutations (N-terminal mutation, non-transmembrane domain) (Lahti A L, et al., *Dis Model Mech.* 2012; 5:220-230) demonstrated 72% and 43% reduction in $I_{Kr}$ currents, which corroborated with their reported arrhythmogenic frequencies of 66% and 5% respectively.

Reduced amplitude of $I_{Kr}$ currents in LQTS2-CMs may be due to impaired channel conductance as well as decreased presence of sarcolemmal hERG channels. The observed reduced membrane hERG by immunostaining and western blots corroborate well with these drastically reduced $I_{Kr}$ currents (80-90%). Such reduction of functional hERG would translate to prolonged APD/cFPD and arrhythmogenesis (75%). Similar to our observations, studies with A614V and R176W mutations showed 72% and 43% $I_{Kr}$ currents reduction that corroborated their arrhythmogenic frequencies of 66% and 5% respectively.

Heterologous expression systems (Ficker E, et al., *Journal of molecular and cellular cardiology* 2000; 32:2327-2337; Kagan A, et al., *J Biol Chem* 2000; 275:11241-11248) have implicated that ER-sequestering of hERG (Thomas D, et al., *Cardiovascular research* 2003; 60:235-241; Ficker E, et al., *Journal of molecular and cellular cardiology* 2000; 32:2327-2337) as a probable cause of LQTS2 manifestation, though the mechanistic pathways in cardiomyocytes remained unclear. Our results support the observations that in healthy CMs, hERG in ER is tagged with HSP70, folded by HSP90 and routed to the sarcolemma via the Golgi complex (Thomas D, et al., *Cardiovascular research* 2003; 60:235-241). To maintain healthy sarcolemmal hERG turnover, CAV3 works along Nedd4-2 (Guo J, et al., *J Biol Chem* 2012; 287:33132-33141) in concert with reduced levels of CAPN1 and CAPN2. However, in LQTS2-CMs, CAPN1 and CAPN2 (well-known in cardiovascular diseases (Sorimachi H, et al., *Cardiovascular research* 2012; 96:11-22) and linked to cell death (Goncalves I, et al., *BMC cardiovascular disorders* 2009; 9:26; Gill C, et al., *FASEB journal: official publication of the Federation of American Societies for Experimental Biology* 2002; 16:135-146)) were upregulated, though their inhibitor, calpastatin (Smith M A, et al., *Cardiovascular research* 2012; 96:32-37), suppresses activation of calpains and prevents cell death. Furthermore, heightened expression of HSPs, UBB and CAV3 indicates elevated proteasomal activity as a result of misprocessed/sequestered hERG due to A561V mutation.

Unlike LQTS2-CMs, such changes were not observed in undifferentiated LQTS2-hiPSCs or patient fibroblasts, suggesting expression of hERG channels and their defective trafficking is primarily manifested in cardiomyocytes, but not necessarily in other cell types. Comparing to cardiomyocytes, hERG expressed by heterologous systems is often present at supraphysiological levels that may skew its relationship with the normal trafficking machinery (Bellin M, et al., *EMBO J* 2013; 32:3161-3175). Such idiosyncratic responses in cardiomyocytes suggest that non-cardiac heterologous expression systems of hERG may not be ideal in representing bona fide cardiac channelopathies. Our results support that A561V mutant of LQTS2, similar to the majority of other known hERG mutations, may be manifesting through defective channel trafficking (Thomas D, et al., *Cardiovascular research* 2003; 60:235-241).

To reverse the trafficking-induced defects, LQTS2-CMs treated with ALLN blocked calpain and proteosomal complex, reducing HSP70 and CAV3 expression levels, indicative of attenuated hERG tagging (Thomas D, et al., *Cardiovascular research* 2003; 60:235-241; Ficker E, et al., *Circulation research* 2003; 92:e87-100) and reduced turnover (Guo J, et al., *J Biol Chem* 2012; 287:33132-33141) respectively. This resulted in misfolded hERG escaping HSP70/90 checkpoints and being re-trafficked to the membrane. Indeed, changes in the HSP70/90 relationship and associated ubiquitination in channel maturation of hERG mutants have been previously demonstrated (Iwai C, et al., *Cardiovascular research* 2013; 100:520-528). This together with decreased CAV3-mediated hERG turnover resulted in an increased sarcolemmal hERG and may result in an increased retention of glycosylated hERG as shown by our western blots.

In this study we, for the first time, demonstrate that functionality of the re-trafficked hERG channels by ALLN was able to increase $I_{Kr}$ currents and reduce cFPD in the LQTS2-CMs with alleviated spontaneous arrythymogenic episodes by voltage-clamp and MEA studies. While $V_{1/2}$ activation did not change significantly, the slope factor of activation was significantly modified, demonstrating alterations of the hERG channel gating kinetics by A561V mutation and its reversal by ALLN treatment.

The mechanism of differential KCNH2 allelic dominance observed in this study remains unclear. Selective expression of mutant allele in hiPSC-CMs, but not undifferentiated hiPSC, would likely accentuate the dominant-negative effect of this A561V mutant. It is uncertain if our observation of such cell-type specific activation pattern of allelic gene expression has a role in phenotypic heterogeneity of LQTS2. Nevertheless, previous studies had indicated that gene dosage as one of the important determinants of LQTS2 phenotype (Priori S G, et al., *Circulation* 1999; 99:518-528), which along with other unidentified modifiers, may contribute to differential clinical penetrance of the disease that warrants specific attention in future studies.

Pharmacological re-trafficking of sequestered hERG by ALLN, as demonstrated in our study, could be useful clinically, as similar re-routing strategy against misfolded F508del-CFTR in cystic fibrosis has been promising and entered Phase 3 clinical trial recently. In summary, we demonstrate the ability of hiPSC technology to recapitulate LQTS2 phenotype in vitro. Ion channel modulators and pharmacological chaperones have proven ineffective in modulating disruption of hERG function by A561V mutation (altered pore stability (Bellocq C, et al., *Mol Pharmacol* 2004; 66:1093-1102)). Our results on re-trafficking of hERG demonstrate an alternative strategy that intervenes prolonged repolarization durations and suppresses arrhythmogenesis in LQTS2-CMs. ALLN as a broad-spectrum inhibitor of the ubiquitin-proteasome pathway may open a platform for developing specific cellular targets, such as HSP70 (Leu J I, et al., *Mol Cell* 2009; 36:15-27), along the trafficking pathway of hERG. This strategy may have an advantage in targeting re-trafficable KCNH2 missense mutations in non-pore forming regions of hERG channel that represent the majority of LQTS2 mutations (Thomas D, et al., *Cardiovascular research* 2003; 60:235-241), as well as other channelopathies that are attributable to similar trafficking defects.

Throughout this specification, unless the context requires otherwise, the word “comprise” or variations such as “comprises” or “comprising”, will be understood to imply the inclusion of a stated element or integer or method step or group of elements or integers or method steps but not the exclusion of any element or integer or method step or group of elements or integers or method steps. In this regard “comprises” includes within its scope “consists essentially of” and “consists of” the stated features.

Reference to any prior art in this specification is not, and should not be taken as, an acknowledgment or any form of suggestion that this prior art forms part of the common general knowledge in any country.

REFERENCES

Anderson C L, Delisle B P, Anson B D, Kilby J A, Will M L, Tester D J, Gong Q, Zhou Z, Ackerman M J, January C T. Most LQT2 mutations reduce Kv11.1 (hERG) current by a class 2 (trafficking-deficient) mechanism. *Circulation* 2006; 113:365-373.

Bellin M, Casini S, Davis R P, D'Aniello C, Haas J, Ward-van Oostwaard D, Tertoolen L G, Jung C B, Elliott D A, Welling A, Laugwitz K L, Moretti A, Mummery C L. Isogenic human pluripotent stem cell pairs reveal the role of a KCNH2 mutation in long-QT syndrome. *EMBO J* 2013; 32:3161-3175.

Bellocq C, Wilders R, Schott J J, Louerat-Oriou B, Boisseau P, Le Marec H, Escande D, Baro I. A common antitussive drug, clobutinol, precipitates the long QT syndrome 2. *Mol Pharmacol* 2004; 66:1093-1102.

Dausse E, Berthet M, Denjoy I, Andre-Fouet X, Cruaud C, Bennaceur M, Faure S, Coumel P, Schwartz K, Guicheney P. A mutation in HERG associated with notched T waves in long QT syndrome. *Journal of molecular and cellular cardiology* 1996; 28:1609-1615.

Elbashir S M, Harborth J, Weber K, Tuschl T. Analysis of gene function in somatic mammalian cells using small interfering RNAs. *Methods* 2002; 26(2):199-213.

Ficker E, Dennis A T, Obejero-Paz C A, Castaldo P, Taglialatela M, Brown A M. Retention in the endoplasmic reticulum as a mechanism of dominant-negative current suppression in human long QT syndrome. *Journal of molecular and cellular cardiology* 2000; 32:2327-2337.

Ficker E, Dennis A T, Wang L, Brown A M. Role of the cytosolic chaperones Hsp70 and Hsp90 in maturation of the cardiac potassium channel HERG. *Circulation research* 2003; 92:e87-100.

Gill C, Mestril R, Samali A. Losing heart: the role of apoptosis in heart disease—a novel therapeutic target? *FASEB journal*: official publication of the Federation of American Societies for Experimental Biology 2002; 16:135-146.

Goncalves I, Nitulescu M, Saido T C, Dias N, Pedro L M, J F E F, Ares M P, Porn-Ares I. Activation of calpain-1 in human carotid artery atherosclerotic lesions. *BMC cardiovascular disorders* 2009; 9:26.

Guo J, Wang T, Li X, Shallow H, Yang T, Li W, Xu J, Fridman M D, Yang X, Zhang S. Cell Surface Expression of Human Ether-a-go-go-related Gene (hERG) Channels Is Regulated by Caveolin-3 Protein via the Ubiquitin Ligase Nedd4-2. *J Biol Chem* 2012; 287:33132-33141.

Itzhaki I, Maizels L, Huber I, Zwi-Dantsis L, Caspi O, Winterstern A, Feldman O, Gepstein A, Arbel G, Hammerman H, Boulos M, Gepstein L. Modelling the long QT syndrome with induced pluripotent stem cells. *Nature* 2011; 471:225-229.

Iwai C, Li P, Kurata Y, Hoshikawa Y, Morikawa K, Maharani N, Higaki K, Sasano T, Notsu T, Ishido Y, Miake J, Y. Y, Shirayoshi Y, Ninorniya H, Nakai A, Murata S, Yoshida A, Yamamoto K, Hiraoka M, Hisatome I. Hsp90 prevents interaction between CHIP and HERG proteins to facilitate maturation of wild-type and mutant HERG proteins. *Cardiovascular research* 2013; 100:520-528.

Kagan A, Yu Z, Fishman G I, McDonald T V. The dominant negative LQT2 mutation A561V reduces wild-type HERG expression. *J Biol Chem* 2000; 275:11241-11248.

Lahti A L, Kujala V J, Chapman H, Koivisto A P, Pekkanen-Mattila M, Kerkela E, Hyttinen J, Kontula K, Swan H, Conklin B R, Yamanaka S, Silvennoinen O, Aalto-Setala K. Model for long qt syndrome type 2 using human ips cells demonstrates arrhythmogenic characteristics in cell culture. *Dis Model Mech.* 2012; 5:220-230.

Leu J I, Pimkina J, Frank A, Murphy M E, George D L. A small molecule inhibitor of inducible heat shock protein 70. *Mol Cell* 2009; 36:15-27.

Matsa E, Rajamohan D, Dick E, Young L, Mellor I, Staniforth A, Denning C. Drug evaluation in cardiomyocytes derived from human induced pluripotent stem cells carrying a long QT syndrome type 2 mutation. *Eur Heart J* 2011; 32:952-962.

Mehta A, Konala V B, Khanna A, Majumdar A S. Assessment of drug induced developmental toxicity using human embryonic stem cells. *Cell Biol Int* 2008; 32: 1412-1424.

Mehta A, Mathew S, Viswanathan C, Sen Majumdar A. Intrinsic properties and external factors determine the differentiation bias of human embryonic stem cell lines. *Cell Biol Int* 2010; 34: 1021-1031.

Mehta A, Chung Y Y, Ng A, Iskandar F, Atan S, Wel H, Dusting G, Sun W, Wong P, Shim W. Pharmacological response of human cardiomyocytes derived from virus-free induced pluripotent stem cells. *Cardiovascular research* 2011; 91:577-586.

Napolitano C, Priori S G, Schwartz P J, Timothy K, Paganini V, Cantu F, Bloise R, De Fusco M, Spazzolini C, Casari G. Identification of a mutational hot spot in HERG-related long QT syndrome (LQT2): phenotypic implications. *Circulation* 1997; 96(suppl I):I-212.

Patel C, Antzelevitch C. Pharmacological approach to the treatment of long and short QT syndromes. *Pharmacology & therapeutics* 2008; 118:138-151.

Priori S G, Barhanin J, Hauer R N, Haverkamp W, Jongsma H J, Kleber A G, McKenna W J, Roden D M, Rudy Y, Schwartz K, Schwartz P J, Towbin J A, Wilde A M. Genetic and molecular basis of cardiac arrhythmias: impact on clinical management parts I and II. *Circulation* 1999; 99:518-528.

Priori S G, Napolitano C, Schwartz P J. Low penetrance in the long-QT syndrome: clinical impact. *Circulation* 1999; 99:529-533.

Sanguinetti M C, Tristani-Firouzi M. hERG potassium channels and cardiac arrhythmia. *Nature* 2006; 440:463-469.

Schwartz P J, Moss A J, Priori S G, Wang Q, Lehmann M H, Timothy K, Denjoy I, Haverkamp W, Guicheney P, Paganini V, Scheinman M M, Karnes P S. Gene-specific influence on the triggers for cardiac arrest in the long QT syndrome. *Circulation* 1997: I-212.

Shieh C C, Coghlan M, Sullivan J P, Gopalakrishnan M. Potassium channels: molecular defects, diseases, and therapeutic opportunities. *Pharmacological reviews* 2000; 52:557-594.

Smith M A, Schnellmann R G. Calpains, mitochondria, and apoptosis. *Cardiovascular research* 2012; 96:32-37.

Sorimachi H, Ono Y. Regulation and physiological roles of the calpain system in muscular disorders. *Cardiovascular research* 2012; 96:11-22.

Thomas D, Kiehn J, Katus H A, Katie C A. Defective protein trafficking in hERG-associated hereditary long QT syndrome (LQT2): molecular mechanisms and restoration of intracellular protein processing. *Cardiovascular research* 2003; 60:235-241.

The invention claimed is:

1. A method of testing compounds for activity in ameliorating long QT syndrome 2 (LQTS2) phenotype, comprising the steps;

(a) contacting LQTS2-specific cardiomyocytes or embryoid bodies (EBs) with a test compound, (b) quantifying the level of human ether-a-go-go related gene (hERG) protein in the endoplasmic reticulum (ER) and in the sarcolemma, and comparing the relative level of hERG in the ER and sarcolemma with untreated cardiomyocytes or EBs, wherein an increase in sarcolemma level and a decrease in ER level of hERG in the treated cells indicates re-trafficking of hERG and the compound has LQTS2-ameliorating activity, (c) quantifying the level of glycosylated (mature) hERG protein and comparing with untreated cardiomyocytes or EBs, wherein increased glycosylation indicates the compound has LQTS2-ameliorating activity, (d) measuring the local field potential duration (FPD), correcting for the beating rate of contracting areas (cFPD), and comparing with untreated cardiomyocytes or EBs, wherein a time-dependent reduction in cFPD indicates the compound has LQTS2-ameliorating activity, and (e) measuring the action potential duration (APD), and comparing with untreated cardiomyocytes or EBs, wherein a time-dependent reduction in APD, indicates the compound has LQTS2-ameliorating activity.

2. The method according to claim 1, further comprising the step; culture LQTS2-specific cardiomyocytes or EBs until spontaneously contracting or induced to contract.

3. The method according to claim 1, wherein the phenotype is cardiac rhythm disturbance, comprising the steps;

(a) culturing LQTS2-specific cardiomyocytes or embryoid bodies (EBs) until spontaneously contracting or induced to contract, (b) contacting the cardiomyocytes or EBs with the test compound, and (i) an agent that triggers arrhythmia, and/or (ii) an agent that increases cardiomyocyte or EB beating rate, (c) measuring the local field potential duration (FPD), correct for the beating rate of contracting areas (cFPD), and compare with untreated cardiomyocytes or EBs, wherein a time-dependent reduction in cFPD indicates the compound has rhythm normalizing activity, and/or (d) measuring the action potential duration (APD), and compare with untreated cardiomyocytes or EBs, wherein a time-dependent reduction in APD indicates the compound has repolarization normalizing activity.

4. The method according to claim 1, comprising the steps;

(a) culturing LQTS2-specific cardiomyocytes or embryoid bodies (EBs) until spontaneously contracting or induced to contract, (b) contacting the cardiomyocytes or EBs with the test compound, and (i) an agent that modulates any one or more of calpain, calpastatin, and ubiquitin expression, and/or (ii) an agent that modulates any one or more of HSP70, HSP90 and CAV3 expression, (c) measuring the local field potential duration (FPD), correct for the beating rate of contracting areas (cFPD), and compare with untreated cardiomyocytes or EBs, wherein a time-dependent reduction in cFPD indicates the compound has LQTS2-ameliorating activity, and/or (d) measuring the action potential duration (APD), and compare with untreated cardiomyocytes or EBs, wherein a time-dependent reduction in APD indicates the compound has LQTS2-ameliorating activity, and/or (e) measuring the hERG channel kinetic and compare with the untreated cardiomyocytes or EBs, wherein a normalizing channel kinetic indicates the compound has LQTS2-ameliorating activity.

5. The method according to claim 4, wherein the HSP70 modulator is any one or more selected from the group consisting of 2 Phenylethynesulfonamide, Pifithrin-μ, 2,5'-thiodipyrimidines, 5-(phenylthio)pyrimidines, 2-(pyridin-3-ylthio)pyrimidines, 3-(phenylthio)pyridines, MKT-077, rapamycin and VER155008.

6. The method according to claim 4, wherein the ubiquitin modulator is any one or more selected from the group consisting of rapamycin, N—[N—(N-Acetyl-L-leucyl)-L-leucyl]-L-norleucine, PYR-41, MLN4924, SMER3, BAY11-7082 and Nutlin-3.

7. The method according to claim 4, wherein the calpain modulator is any one or more selected from the group consisting of 4PBA, N—[N—(N-Acetyl-L-leucyl)-L-leucyl]-L-norleucine, MG-132, 3-[6-[[1-(2,2-difluoro-1,3-benzodioxol-5-yl)cyclopropanecarbonyl]amino]-3-methyl-pyridin-2-yl]benzoic acid, AK275, MDL28170, PD150606, SJA6017, ABT-705253 and SNJ-1945.

8. The method according to claim 4, wherein the CAV3 modulator is SB203580.

9. The method according to claim 4, wherein the HSP90 modulator is any one or more selected from the group consisting of 4 hydroxytamoxifen, tomoxifen, activator of Hsp90 ATPase homolog1 (AHA1).

10. The method according to claim 1, wherein the phenotype is cardiac rhythm instability, comprising the steps;

(a) culturing LQTS2-specific cardiomyocytes or embryoid bodies (EBs) until spontaneously contracting with normal rhythm, (b) contacting the cardiomyocytes or EBs with the test compound, and (i) an agent that increases cardiomyocyte or EB beating rate, and/or (ii) an agent that triggers abnormal cardiac rhythm, (c) measuring the local field potential duration (FPD), correct for the beating rate of contracting areas (cFPD), and compare with untreated cardiomyocytes or EBs, wherein a time-dependent reduction in cFPD indicates the compound has rhythm normalizing activity, and/or (d) measuring the action potential duration (APD), and compare with untreated cardiomyocytes or EBs, wherein a time-dependent reduction in APD indicates the compound has repolarization normalizing activity, and/or (e) measuring the presence of early after-depolarizations (EADs) and compare to untreated cardiomyocytes or EBs, wherein the suppression of EADs indicates the compound has arrhythmia suppressing activity.

11. The method according to claim 10, wherein the agent that increases cardiomyocyte or EB beating rate is any one or more selected from the group consisting of isoprenaline, dobutamine, epinephrine, norepinephrine and xamoterol.

12. The method according to claim 10, wherein the agent that triggers abnormal cardiac rhythm is any one or more selected from the group consisting of E-4031, terfenadine, roxithromycin, fluconazole, cisapride and astemizole.

* * * * *

SEQUENCE LISTING

```
<160> NUMBER OF SEQ ID NOS: 71

<210> SEQ ID NO 1
<211> LENGTH: 19
<212> TYPE: DNA
<213> ORGANISM: Artificial Sequence
<220> FEATURE:
<223> OTHER INFORMATION: KCHN2 (Seq) forward primer

<400> SEQUENCE: 1

atgacgcaga tggagaaga                                               19


<210> SEQ ID NO 2
<211> LENGTH: 20
<212> TYPE: DNA
<213> ORGANISM: Artificial Sequence
<220> FEATURE:
<223> OTHER INFORMATION: KCHN2 (RE) forward primer
```

<400> SEQUENCE: 2
ctgatcgggc tgctgaagac 20

<210> SEQ ID NO 3
<211> LENGTH: 19
<212> TYPE: DNA
<213> ORGANISM: Artificial Sequence
<220> FEATURE:
<223> OTHER INFORMATION: KCHN2 (RE) reverse primer

<400> SEQUENCE: 3
agccaatgag catgacgca 19

<210> SEQ ID NO 4
<211> LENGTH: 20
<212> TYPE: DNA
<213> ORGANISM: Artificial Sequence
<220> FEATURE:
<223> OTHER INFORMATION: KCHN2 (AS)-Wt forward primer

<400> SEQUENCE: 4
tgcacctttg cgctcatccc 20

<210> SEQ ID NO 5
<211> LENGTH: 23
<212> TYPE: DNA
<213> ORGANISM: Artificial Sequence
<220> FEATURE:
<223> OTHER INFORMATION: KCHN2 (AS)-Wt reverse primer

<400> SEQUENCE: 5
gcgccgtcac atacttgtcc ttg 23

<210> SEQ ID NO 6
<211> LENGTH: 20
<212> TYPE: DNA
<213> ORGANISM: Artificial Sequence
<220> FEATURE:
<223> OTHER INFORMATION: KCHN2 (AS)-Mt forward primer

<400> SEQUENCE: 6
tgcacctttg cgctcatcct 20

<210> SEQ ID NO 7
<211> LENGTH: 23
<212> TYPE: DNA
<213> ORGANISM: Artificial Sequence
<220> FEATURE:
<223> OTHER INFORMATION: KCHN2 (AS)-Mt reverse primer

<400> SEQUENCE: 7
gcgccgtcac atacttgtcc ttg 23

<210> SEQ ID NO 8
<211> LENGTH: 21
<212> TYPE: DNA
<213> ORGANISM: Artificial Sequence
<220> FEATURE:
<223> OTHER INFORMATION: KCHN2 (AS)-Total forward primer

<400> SEQUENCE: 8
cgtgctgcct gagtacaagc t 21

<210> SEQ ID NO 9
<211> LENGTH: 23

<212> TYPE: DNA
<213> ORGANISM: Artificial Sequence
<220> FEATURE:
<223> OTHER INFORMATION: KCHN2 (AS)-Total reverse primer

<400> SEQUENCE: 9
tgtgaagaca gccgtgtaga tga 23

<210> SEQ ID NO 10
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 10
gtggacctga cctgccgtct 20

<210> SEQ ID NO 11
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 11
ggaggagtgg gtgtcgctgt 20

<210> SEQ ID NO 12
<211> LENGTH: 20
<212> TYPE: DNA
<213> ORGANISM: Artificial Sequence
<220> FEATURE:
<223> OTHER INFORMATION: Oct-4 forward primer

<400> SEQUENCE: 12
agtttgtgcc agggtttttg 20

<210> SEQ ID NO 13
<211> LENGTH: 20
<212> TYPE: DNA
<213> ORGANISM: Artificial Sequence
<220> FEATURE:
<223> OTHER INFORMATION: Oct-4 reverse primer

<400> SEQUENCE: 13
acttcacctt ccctccaacc 20

<210> SEQ ID NO 14
<211> LENGTH: 20
<212> TYPE: DNA
<213> ORGANISM: Artificial Sequence
<220> FEATURE:
<223> OTHER INFORMATION: Sox-2 forward primer

<400> SEQUENCE: 14
aaaaatccca tcacccacag 20

<210> SEQ ID NO 15
<211> LENGTH: 19
<212> TYPE: DNA
<213> ORGANISM: Artificial Sequence
<220> FEATURE:
<223> OTHER INFORMATION: Sox-2 reverse primer

<400> SEQUENCE: 15
gcggtttttg cgtgagtgt 19

<210> SEQ ID NO 16
<211> LENGTH: 20
<212> TYPE: DNA
<213> ORGANISM: Artificial Sequence
<220> FEATURE:
<223> OTHER INFORMATION: Nanog forward primer

<400> SEQUENCE: 16
ctccatgaac atgcaacctg 20

<210> SEQ ID NO 17
<211> LENGTH: 20
<212> TYPE: DNA
<213> ORGANISM: Artificial Sequence
<220> FEATURE:
<223> OTHER INFORMATION: Nanog reverse primer

<400> SEQUENCE: 17
gaggaaggat tcagccagtg 20

<210> SEQ ID NO 18
<211> LENGTH: 20
<212> TYPE: DNA
<213> ORGANISM: Artificial Sequence
<220> FEATURE:
<223> OTHER INFORMATION: hTert forward primer

<400> SEQUENCE: 18
tggcaggtgt acggcttcgt 20

<210> SEQ ID NO 19
<211> LENGTH: 20
<212> TYPE: DNA
<213> ORGANISM: Artificial Sequence
<220> FEATURE:
<223> OTHER INFORMATION: hTert reverse primer

<400> SEQUENCE: 19
cagctcctgc agcgagagct 20

<210> SEQ ID NO 20
<211> LENGTH: 20
<212> TYPE: DNA
<213> ORGANISM: Artificial Sequence
<220> FEATURE:
<223> OTHER INFORMATION: Nestin forward primer

<400> SEQUENCE: 20
caggagaaac agggcctaca 20

<210> SEQ ID NO 21
<211> LENGTH: 20
<212> TYPE: DNA
<213> ORGANISM: Artificial Sequence
<220> FEATURE:
<223> OTHER INFORMATION: Nestin reverse primer

<400> SEQUENCE: 21
taagaaaggc tggcacaggt 20

<210> SEQ ID NO 22
<211> LENGTH: 20
<212> TYPE: DNA
<213> ORGANISM: Artificial Sequence
<220> FEATURE:
<223> OTHER INFORMATION: Pax 6 forward primer

<400> SEQUENCE: 22
ccggcagaag attgtagagc 20

<210> SEQ ID NO 23
<211> LENGTH: 20
<212> TYPE: DNA
<213> ORGANISM: Artificial Sequence
<220> FEATURE:
<223> OTHER INFORMATION: Pax 6 reverse primer

<400> SEQUENCE: 23
ctagccaggt tgcgaagaac 20

<210> SEQ ID NO 24
<211> LENGTH: 20
<212> TYPE: DNA
<213> ORGANISM: Artificial Sequence
<220> FEATURE:
<223> OTHER INFORMATION: AFP forward primer

<400> SEQUENCE: 24
ccgaactttc caagccataa 20

<210> SEQ ID NO 25
<211> LENGTH: 20
<212> TYPE: DNA
<213> ORGANISM: Artificial Sequence
<220> FEATURE:
<223> OTHER INFORMATION: AFP reverse primer

<400> SEQUENCE: 25
tggcattcaa gagggttttc 20

<210> SEQ ID NO 26
<211> LENGTH: 20
<212> TYPE: DNA
<213> ORGANISM: Artificial Sequence
<220> FEATURE:
<223> OTHER INFORMATION: HNF4-alpha forward primer

<400> SEQUENCE: 26
caggctcaag aaatgcttcc 20

<210> SEQ ID NO 27
<211> LENGTH: 20
<212> TYPE: DNA
<213> ORGANISM: Artificial Sequence
<220> FEATURE:
<223> OTHER INFORMATION: HNF4-alpha reverse primer

<400> SEQUENCE: 27
gtgccgaggg acaatgtagt 20

<210> SEQ ID NO 28
<211> LENGTH: 20
<212> TYPE: DNA
<213> ORGANISM: Artificial Sequence
<220> FEATURE:
<223> OTHER INFORMATION: Isl1 forward primer

<400> SEQUENCE: 28
aaggacaaga agagaagcat 20

-continued

<210> SEQ ID NO 29
<211> LENGTH: 20
<212> TYPE: DNA
<213> ORGANISM: Artificial Sequence
<220> FEATURE:
<223> OTHER INFORMATION: Isl1 reverse primer

<400> SEQUENCE: 29
catgggagtt cctgtcatcc 20

<210> SEQ ID NO 30
<211> LENGTH: 20
<212> TYPE: DNA
<213> ORGANISM: Artificial Sequence
<220> FEATURE:
<223> OTHER INFORMATION: GATA4 forward primer

<400> SEQUENCE: 30
tccaaaccag aaaacggaag 20

<210> SEQ ID NO 31
<211> LENGTH: 20
<212> TYPE: DNA
<213> ORGANISM: Artificial Sequence
<220> FEATURE:
<223> OTHER INFORMATION: GATA4 reverse primer

<400> SEQUENCE: 31
aaggctctca ctgcctgaag 20

<210> SEQ ID NO 32
<211> LENGTH: 20
<212> TYPE: DNA
<213> ORGANISM: Artificial Sequence
<220> FEATURE:
<223> OTHER INFORMATION: Nkx2.5 forward primer

<400> SEQUENCE: 32
ctaaacctgg aacagcagca 20

<210> SEQ ID NO 33
<211> LENGTH: 20
<212> TYPE: DNA
<213> ORGANISM: Artificial Sequence
<220> FEATURE:
<223> OTHER INFORMATION: Nkx2.5 reverse primer

<400> SEQUENCE: 33
gtaggcctct ggcttgaagg 20

<210> SEQ ID NO 34
<211> LENGTH: 19
<212> TYPE: DNA
<213> ORGANISM: Artificial Sequence
<220> FEATURE:
<223> OTHER INFORMATION: cTnI forward primer

<400> SEQUENCE: 34
ccaactaccg cgcttatgc 19

<210> SEQ ID NO 35
<211> LENGTH: 20
<212> TYPE: DNA
<213> ORGANISM: Artificial Sequence
<220> FEATURE:
<223> OTHER INFORMATION: cTnI reverse primer

<400> SEQUENCE: 35
ctcgctccag ctcttgcttt 20

<210> SEQ ID NO 36
<211> LENGTH: 18
<212> TYPE: DNA
<213> ORGANISM: Artificial Sequence
<220> FEATURE:
<223> OTHER INFORMATION: MLC2v forward primer

<400> SEQUENCE: 36
ccttgggcga gtgaacgt 18

<210> SEQ ID NO 37
<211> LENGTH: 20
<212> TYPE: DNA
<213> ORGANISM: Artificial Sequence
<220> FEATURE:
<223> OTHER INFORMATION: MLC2v reverse primer

<400> SEQUENCE: 37
gggtccgctc ccttaagttt 20

<210> SEQ ID NO 38
<211> LENGTH: 21
<212> TYPE: DNA
<213> ORGANISM: Artificial Sequence
<220> FEATURE:
<223> OTHER INFORMATION: MYH7 forward primer

<400> SEQUENCE: 38
ggcaagacag tgaccgtgaa g 21

<210> SEQ ID NO 39
<211> LENGTH: 22
<212> TYPE: DNA
<213> ORGANISM: Artificial Sequence
<220> FEATURE:
<223> OTHER INFORMATION: MYH7 reverse primer

<400> SEQUENCE: 39
cgtagcgatc cttgaggttg ta 22

<210> SEQ ID NO 40
<211> LENGTH: 23
<212> TYPE: DNA
<213> ORGANISM: Artificial Sequence
<220> FEATURE:
<223> OTHER INFORMATION: CACNA1d forward primer

<400> SEQUENCE: 40
gggcaatggg acctcataaa taa 23

<210> SEQ ID NO 41
<211> LENGTH: 22
<212> TYPE: DNA
<213> ORGANISM: Artificial Sequence
<220> FEATURE:
<223> OTHER INFORMATION: CACNA1D reverse primer

<400> SEQUENCE: 41
ttacctggtt gcgagtgcat ta 22

<210> SEQ ID NO 42

<211> LENGTH: 21
<212> TYPE: DNA
<213> ORGANISM: Artificial Sequence
<220> FEATURE:
<223> OTHER INFORMATION: HCN4 forward primer

<400> SEQUENCE: 42
gaccgcattg gcaagaagaa c 21

<210> SEQ ID NO 43
<211> LENGTH: 18
<212> TYPE: DNA
<213> ORGANISM: Artificial Sequence
<220> FEATURE:
<223> OTHER INFORMATION: HCN4 reverse primer

<400> SEQUENCE: 43
gggccatctc ccggtcat 18

<210> SEQ ID NO 44
<211> LENGTH: 20
<212> TYPE: DNA
<213> ORGANISM: Artificial Sequence
<220> FEATURE:
<223> OTHER INFORMATION: CAPN1 forward primer

<400> SEQUENCE: 44
ccaagcaggt gaactaccga 20

<210> SEQ ID NO 45
<211> LENGTH: 20
<212> TYPE: DNA
<213> ORGANISM: Artificial Sequence
<220> FEATURE:
<223> OTHER INFORMATION: CAPN1 reverse primer

<400> SEQUENCE: 45
ggtccacgtt gttccactct 20

<210> SEQ ID NO 46
<211> LENGTH: 20
<212> TYPE: DNA
<213> ORGANISM: Artificial Sequence
<220> FEATURE:
<223> OTHER INFORMATION: CAPN2 forward primer

<400> SEQUENCE: 46
gcaggaacta cccgaacaca 20

<210> SEQ ID NO 47
<211> LENGTH: 20
<212> TYPE: DNA
<213> ORGANISM: Artificial Sequence
<220> FEATURE:
<223> OTHER INFORMATION: CAPN2 reverse primer

<400> SEQUENCE: 47
tgcttctgaa tgagccccac 20

<210> SEQ ID NO 48
<211> LENGTH: 20
<212> TYPE: DNA
<213> ORGANISM: Artificial Sequence
<220> FEATURE:
<223> OTHER INFORMATION: CAPN3 forward primer

<400> SEQUENCE: 48
gtcaacgacg caggattcca 20

<210> SEQ ID NO 49
<211> LENGTH: 20
<212> TYPE: DNA
<213> ORGANISM: Artificial Sequence
<220> FEATURE:
<223> OTHER INFORMATION: CAPN3 reverse primer

<400> SEQUENCE: 49
gaacatgccc tccagcctaa 20

<210> SEQ ID NO 50
<211> LENGTH: 20
<212> TYPE: DNA
<213> ORGANISM: Artificial Sequence
<220> FEATURE:
<223> OTHER INFORMATION: CAST forward primer

<400> SEQUENCE: 50
ctgcaatatc tggcaagccg 20

<210> SEQ ID NO 51
<211> LENGTH: 20
<212> TYPE: DNA
<213> ORGANISM: Artificial Sequence
<220> FEATURE:
<223> OTHER INFORMATION: CAST reverse primer

<400> SEQUENCE: 51
atccatgcct gactttcccg 20

<210> SEQ ID NO 52
<211> LENGTH: 21
<212> TYPE: DNA
<213> ORGANISM: Artificial Sequence
<220> FEATURE:
<223> OTHER INFORMATION: CAV3 forward primer

<400> SEQUENCE: 52
ctttgacggc gtgtggaagg t 21

<210> SEQ ID NO 53
<211> LENGTH: 19
<212> TYPE: DNA
<213> ORGANISM: Artificial Sequence
<220> FEATURE:
<223> OTHER INFORMATION: CAV3 reverse primer

<400> SEQUENCE: 53
accgcccaga tgtggcaga 19

<210> SEQ ID NO 54
<211> LENGTH: 20
<212> TYPE: DNA
<213> ORGANISM: Artificial Sequence
<220> FEATURE:
<223> OTHER INFORMATION: HSP70 forward primer

<400> SEQUENCE: 54
ggtataagag gcagggtggc 20

<210> SEQ ID NO 55
<211> LENGTH: 20
<212> TYPE: DNA

<213> ORGANISM: Artificial Sequence
<220> FEATURE:
<223> OTHER INFORMATION: HSP70 reverse primer

<400> SEQUENCE: 55
gacatggttg ctggggtgta 20

<210> SEQ ID NO 56
<211> LENGTH: 20
<212> TYPE: DNA
<213> ORGANISM: Artificial Sequence
<220> FEATURE:
<223> OTHER INFORMATION: HSP90 forward primer

<400> SEQUENCE: 56
atgattggcc agttcggtgt 20

<210> SEQ ID NO 57
<211> LENGTH: 20
<212> TYPE: DNA
<213> ORGANISM: Artificial Sequence
<220> FEATURE:
<223> OTHER INFORMATION: HSP90 reverse primer

<400> SEQUENCE: 57
ggttcacctg tgtctgtcct 20

<210> SEQ ID NO 58
<211> LENGTH: 20
<212> TYPE: DNA
<213> ORGANISM: Artificial Sequence
<220> FEATURE:
<223> OTHER INFORMATION: UBB forward primer

<400> SEQUENCE: 58
atttaggggc ggttggcttt 20

<210> SEQ ID NO 59
<211> LENGTH: 21
<212> TYPE: DNA
<213> ORGANISM: Artificial Sequence
<220> FEATURE:
<223> OTHER INFORMATION: UBB reverse primer

<400> SEQUENCE: 59
tgcattttga cctgttagcg g 21

<210> SEQ ID NO 60
<211> LENGTH: 20
<212> TYPE: DNA
<213> ORGANISM: Artificial Sequence
<220> FEATURE:
<223> OTHER INFORMATION: Oct-4 genomic forward primer

<400> SEQUENCE: 60
agtgagaggc aacctggaga 20

<210> SEQ ID NO 61
<211> LENGTH: 20
<212> TYPE: DNA
<213> ORGANISM: Artificial Sequence
<220> FEATURE:
<223> OTHER INFORMATION: Oct-4 genomic reverse primer

<400> SEQUENCE: 61
aggaactgct tccttcacga 20

<210> SEQ ID NO 62
<211> LENGTH: 20
<212> TYPE: DNA
<213> ORGANISM: Artificial Sequence
<220> FEATURE:
<223> OTHER INFORMATION: Nanog genomic forward primer

<400> SEQUENCE: 62
cagaaggcct cagcacctac 20

<210> SEQ ID NO 63
<211> LENGTH: 20
<212> TYPE: DNA
<213> ORGANISM: Artificial Sequence
<220> FEATURE:
<223> OTHER INFORMATION: Nanog genomic reverse primer

<400> SEQUENCE: 63
aggaactgct tccttcacga 20

<210> SEQ ID NO 64
<211> LENGTH: 20
<212> TYPE: DNA
<213> ORGANISM: Artificial Sequence
<220> FEATURE:
<223> OTHER INFORMATION: c-Myc genomic forward primer

<400> SEQUENCE: 64
tcaagaggcg aacacacaac 20

<210> SEQ ID NO 65
<211> LENGTH: 20
<212> TYPE: DNA
<213> ORGANISM: Artificial Sequence
<220> FEATURE:
<223> OTHER INFORMATION: c-Myc genomic reverse primer

<400> SEQUENCE: 65
aggaactgct tccttcacga 20

<210> SEQ ID NO 66
<211> LENGTH: 20
<212> TYPE: DNA
<213> ORGANISM: Artificial Sequence
<220> FEATURE:
<223> OTHER INFORMATION: Sox-2 genomic forward primer

<400> SEQUENCE: 66
accagctcgc agacctacat 20

<210> SEQ ID NO 67
<211> LENGTH: 20
<212> TYPE: DNA
<213> ORGANISM: Artificial Sequence
<220> FEATURE:
<223> OTHER INFORMATION: Sox-2 genomic reverse primer

<400> SEQUENCE: 67
ccccctgaac ctgaaacata 20

<210> SEQ ID NO 68
<211> LENGTH: 20
<212> TYPE: DNA
<213> ORGANISM: Artificial Sequence
<220> FEATURE:

-continued

```
<223> OTHER INFORMATION: KLF4 genomic forward primer

<400> SEQUENCE: 68

cccacacagg tgagaaacct                                        20


<210> SEQ ID NO 69
<211> LENGTH: 20
<212> TYPE: DNA
<213> ORGANISM: Artificial Sequence
<220> FEATURE:
<223> OTHER INFORMATION: KLF4 genomic reverse primer

<400> SEQUENCE: 69

cccccctgaac ctgaaacata                                       20


<210> SEQ ID NO 70
<211> LENGTH: 20
<212> TYPE: DNA
<213> ORGANISM: Artificial Sequence
<220> FEATURE:
<223> OTHER INFORMATION: EBNA-1 genomic forward primer

<400> SEQUENCE: 70

atcgtcaaag ctgcacacag                                        20


<210> SEQ ID NO 71
<211> LENGTH: 20
<212> TYPE: DNA
<213> ORGANISM: Artificial Sequence
<220> FEATURE:
<223> OTHER INFORMATION: EBNA-1 genomic reverse primer

<400> SEQUENCE: 71

cccaggagtc ccagtagtca                                        20
```